(12) United States Patent
Hajduk et al.

(10) Patent No.: US 6,535,284 B1
(45) Date of Patent: Mar. 18, 2003

(54) RHEO-OPTICAL INDEXER AND METHOD OF SCREENING AND CHARACTERIZING ARRAYS OF MATERIALS

(75) Inventors: Damian Hajduk, San Jose, CA (US); Eric Carlson, Palo Alto, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/579,338

(22) Filed: May 25, 2000

Related U.S. Application Data

(63) Continuation-in-part of application No. 09/174,986, filed on Oct. 19, 1998, now Pat. No. 6,157,449.

(51) Int. Cl.[7] .................................................. G01J 4/00
(52) U.S. Cl. ........................ 356/367; 356/364; 356/244; 356/246
(58) Field of Search ............................... 356/244, 246, 356/364, 366, 33, 36, 367; 422/104, 82.05; 435/288.4; 436/150; 250/225

(56) References Cited

U.S. PATENT DOCUMENTS

| | | | |
|---|---|---|---|
| 4,749,854 A | 6/1988 | Martens | 250/225 |
| 5,239,365 A | 8/1993 | Inoue | 356/367 |
| 5,257,092 A | 10/1993 | Noguchi et al. | 356/367 |
| 5,311,284 A | 5/1994 | Nishino | 356/364 |
| 5,694,205 A | 12/1997 | Gualtieri et al. | 356/33 |
| 5,776,359 A | 7/1998 | Schultz et al. | |
| 5,788,632 A | 8/1998 | Pezzaniti et al. | 600/316 |
| 5,959,297 A | 9/1999 | Weinberg et al. | |
| 6,004,617 A | 12/1999 | Schultz et al. | |
| 6,030,917 A | 2/2000 | Weinberg et al. | |
| 6,031,614 A | 2/2000 | Michaelis et al. | 356/369 |
| 6,034,775 A | 3/2000 | McFarland et al. | |
| 6,048,723 A | * 4/2000 | Banes | 435/288.3 |
| 6,087,181 A | 7/2000 | Cong | |
| 6,149,882 A | 11/2000 | Guan et al. | |
| 6,151,123 A | 11/2000 | Nielsen | |
| 6,157,449 A | * 12/2000 | Hajduk | 356/364 |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,225,487 B1 | 5/2001 | Guram | |
| 6,260,407 B1 | 7/2001 | Petro et al. | |
| 6,265,226 B1 | 7/2001 | Petro et al. | |
| 6,294,388 B1 | 9/2001 | Petro | |
| 6,296,771 B1 | 10/2001 | Miroslav | |

\* cited by examiner

*Primary Examiner*—Frank G. Font
*Assistant Examiner*—Roy M. Punnoose
(74) *Attorney, Agent, or Firm*—Dobrusin & Thennisch PC

(57) ABSTRACT

A method and apparatus for characterizing and screening an array of material samples is disclosed. The apparatus includes a sample block having a plurality of regions for containing the material samples, a polarized light source to illuminate the materials, an analyzer having a polarization direction different than the polarization direction of the polarized light source, and a detector for analyzing changes in the intensity of the light beams. The light source, together with a polarizer, may include a plurality of light beams to simultaneously illuminate the entire array of materials with linearly polarized light so that characterization and screening can be performed in parallel. In addition, the materials in the sample block maybe subjected to different environmental conditions or mechanical stresses, and the detector analyzes the array as a function of the different environmental conditions or mechanical stresses.

33 Claims, 17 Drawing Sheets

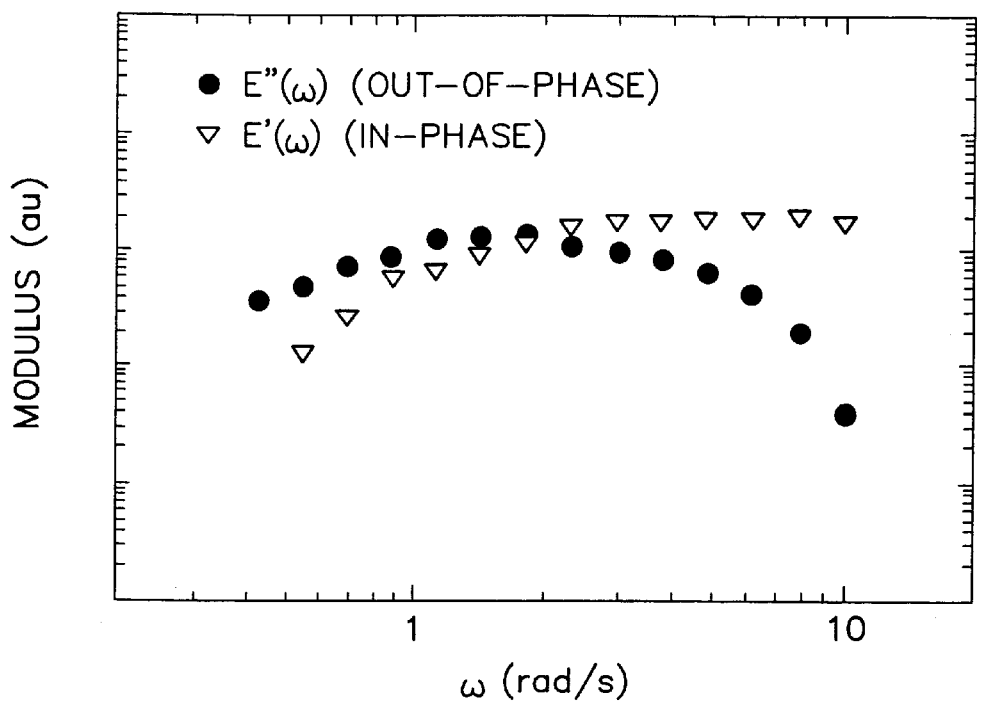
FIG. 22  POLYISOBUTYLENE
$M_w = 86,100$ g/mol
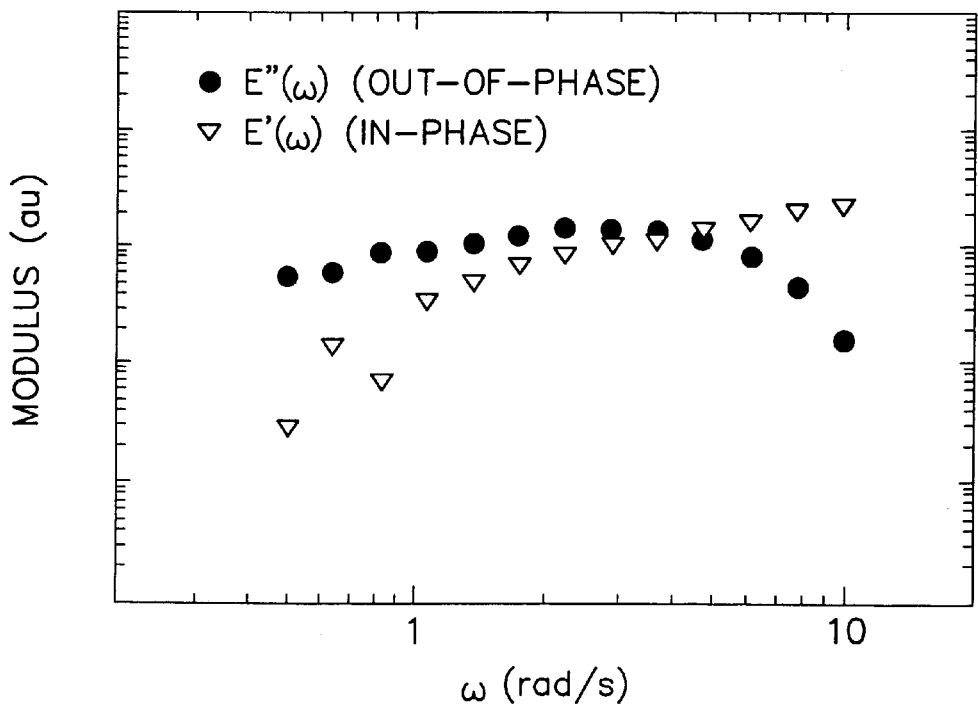
FIG. 23  POLYISOBUTYLENE
$M_w = 73,200$ g/mol

RHEO-OPTICAL INDEXER AND METHOD OF SCREENING AND CHARACTERIZING ARRAYS OF MATERIALS

CROSS-REFERENCE TO RELATED APPLICATION

This application is a continuation-in-part of Ser. No. 09/174,986, filed Oct. 19, 1998, now U.S. Pat. No. 6,157,449.

BACKGROUND

1. Technical Field

The present invention relates to a method and apparatus for rapidly screening and characterizing an array of materials, and more particularly, to an optical device and technique for simultaneously measuring rheological properties of a combinatorial library of materials.

2. Discussion

Combinatorial chemistry generally refers to methods and materials for creating collections of diverse materials or compounds—commonly known as libraries—and to techniques and instruments for evaluating or screening libraries for desirable properties. Combinatorial chemistry has revolutionized the process of drug discovery, and has enabled researchers to rapidly discover and optimize useful materials such as superconductors, zeolites, magnetic materials, phosphors, catalysts, thermoelectric materials, and high and low dielectric materials.

Analytical techniques that rely on serial measurements of individual library members are often unsuitable for screening combinatorial libraries. Because combinatorial libraries routinely comprise hundreds or thousands of individual library members, viable serial screening techniques require sampling times of a few minutes or less. Although serial techniques can use automation to speed up processing, many sophisticated analytical instruments have relatively long response times, making such instruments impractical for use as screening tools.

Parallel methods represent a useful approach for attaining the requisite sample throughput. Whereas serial screening techniques require instruments having short response times, parallel techniques achieve the necessary sample throughput by measuring one or more properties of all library members simultaneously. Parallel methods can thus use instruments having comparatively sluggish response times. However, the success of any parallel screening method depends strongly on the screening criteria and the information provided by the particular technique.

Optical screening methods possess certain advantages over other techniques because one may adapt existing imaging and image processing technologies for parallel data collection and analysis. Optical characteristics of a compound or material often reveal the electronic properties and spatial arrangement of constituent molecules, making it possible to detect changes in physical or chemical structure through optical measurements. For example, optical measurements have been used to screen for selected characteristics of materials as a function of applied voltage. See, U.S. Pat. No. 6,034,775 and U.S. patent application "Method and Apparatus for Screening Combinatorial Libraries for Semi-Conducting Properties," Ser. No. 09/414,615, which are herein incorporated by reference.

Thus, there exists a need for other devices and methods for rapidly screening and characterizing, in parallel, optical and physical properties of an array of compounds or materials.

SUMMARY OF THE INVENTION

The present invention provides an apparatus for screening an array of at least partially transparent material samples in a combinatorial library, the material samples exhibiting changes in birefringence as a function of environmental conditions. The apparatus includes a sample block having a plurality of regions therein for receiving the library members. The term sample block is not meant to place any structural limitations (e.g. size or shape) on the invention. The apparatus also includes a light source that provides at least one light beam light that is polarized and directed toward the regions, an analyzer for filtering out light having the same polarization as the incident light beam after it passes through the regions, and a detector for analyzing changes in the intensity of the light beams due to the optical characteristics of the library members. The sample block, light source, analyzer and detector are all arranged in series.

Preferably, the sample block receives vials of the material samples within the regions formed therein. The vials that receive the library members can be constructed from any material or combination of materials that are at least partially transparent to the light emitted by the source. Suitable materials include glass, quartz, and transparent plastic sheets, which are generally free of residual stresses. These vials should be nonbirefringent; that is, the vials should not alter the polarization characteristics of light that passes through them.

In accordance with one aspect of the invention, the light source preferably includes a plurality of lights, such as light emitting diodes (LEDs) that are all directed toward the regions simultaneously such that the entire array of material samples may be illuminated at once. A polarizer, such as a commercially available polarizing filter or polarizing mirror, is placed between the light source and the regions to polarize the light before it passes through the vials and material samples in the library. The polarized light beams are then collimated, preferably by passing the light beams through a separate collimator plate, to reduce stray light. As the light passes through the material sample, the sample alters the polarization of the light in a manner determined by the structural characteristics of the material sample. Next, the light beams are passed through a second polarizer or an analyzer, the second polarizer having a preferred polarization direction oriented at 90° relative to the first polarizer. The analyzer filters the light beams, only transmitting that fraction of the radiation which has a specific linear polarization.

In accordance with another aspect of the invention, the detector includes a fiber optic assembly and a charged-coupled device (CCD) camera to capture readings of the light intensity transmitted through the material samples. A first fiber optic plate is positioned above the second polarizer and a second fiber optic plate is placed above the first fiber optic plate. A bundle of fiber optics is placed between the plates with the ends of the fibers extending through holes in both plates. Light transmitted through the second polarizer is captured by the fiber ends extending through the first plate, is transmitted through the fibers, emerging at the second plate. The fibers in the bundle are arranged in a tapered configuration so as to reduce the dimensions of the area over which the light is distributed from the array of samples to a size more easily imaged by the CCD camera.

In accordance with another aspect of the invention, the apparatus may also include a temperature-controlled block. The sample block holding the vials of material samples is disposed within the temperature-controlled block such that intensity readings of the material samples may be evaluated as a function of temperature. The apparatus may further include a substantially gas-tight environmental chamber. The sample block holding the vials of material samples is mounted within the substantially gas-tight environmental chamber. At least one gas is directed into the chamber so as to subject the material samples to pressure, wherein intensity readings of the material samples may be evaluated as a function of pressure. Alternatively, the substantially gas-tight environmental chamber may be subject to a continuous mixture of two or more gases so that intensity reading of the material samples may be evaluated as a function of the gas mixture composition.

In accordance with another aspect of the invention, the sample block may further include an array of electrode pairs, wherein a separate electrode pair is associated with each region. The electrode pairs are arranged in an opposing manner, with the region containing the materials disposed there between. A power supply is connected in series with the electrode pairs such that when voltage is applied to the pairs, an electric field is generated across each material sample. The intensity readings of the material samples may then be evaluated as a function of applied voltage.

In accordance with another aspect of the invention, the sample block may further include pairs of electromagnetic devices, wherein a separate electromagnetic device pair is associated with one region. The pairs of electromagnetic devices are arranged in an opposing manner, with the region containing the materials disposed there between. A power supply is connected in series with the pairs of electromagnetic devices such that when voltage is applied, a magnetic field is generated across each material sample. The intensity readings of the material samples may then be evaluated as a function of magnetic field strength.

The present invention also provides a method of characterizing an array of material samples of a combinatorial library comprising providing an array of material samples in transparent sample blocks, e.g. in vials, illuminating at least one material in the array with a beam of polarized light that passes through the vials, filtering out intensity of the polarized light beam that has the same polarization direction as the incident light beam by passing the polarized light beam through an analyzer having a polarization direction oriented at a predetermined angle, (for example and without limitation, 90° with respect to the direction of the polarized light beam), detecting changes in the intensity of the polarized light beam due to the optical characteristics of the material sample and determining characteristics of at least one material based on the detected changes in the intensity values. In a preferred method, polarized light beams are arranged such that the entire array of material samples is illuminated simultaneously.

In accordance with another aspect of the invention, the method may further include determining characteristics of the material samples as a function of various environmental conditions. In one embodiment, the temperature of the material samples is varied such that the detecting and determining steps are performed as a function of temperature. In another embodiment the materials are subject to pressure such that the detecting and determining step are performed as a function of pressure. The material sample may also be continuously subjected to a mixture of gases such that the detecting step may be done as a function of gas composition. Further, the method also may include generating an electric field across each material samples such that the detecting and determining step are performed as a function of applied voltage. In yet another embodiment, the method may include generating a magnetic field across each material sample such that the detecting and determining step are performed as a function of magnetic field strength.

The present invention also provides an apparatus for simultaneously measuring rheological properties of an array of material samples. The apparatus comprises transparent, generally planar first and second surfaces that define a substantially uniform gap for containing the material samples. The apparatus includes a device that moves the first surface relative to the second surface so as to exert a shear stress on the material samples disposed within the gap. The apparatus also includes a light source having a first polarization direction and an analyzer having a second polarization direction. The source of light and the analyzer are located on opposite sides of the gap so that light from the source passes through the material samples contained in the gap before striking the analyzer. A detector, which is located adjacent to the analyzer monitors light that passes through the material samples and the analyzer. The detector is capable of distinguishing light transmitted through at least two of the material samples simultaneously. Normally, the first and second polarization directions are orthogonal, so that in the absence of shear the analyzer completely blocks out light from the material samples. When subject to a shear stress, however, the materials may polarize the light—a phenomenon known as stress-induced birefringence—which appears as a change in the intensity of light exiting the analyzer.

The present invention also provides a method of screening an array of materials based on stress-induced birefringence. The method includes providing an array of materials composed of discrete material elements, which are illuminated with light having a first polarization direction. The method also includes shearing the array of materials by deforming each of the discrete material elements in a direction about normal to the transmission direction of the light, and directing the light from the array of materials through an analyzer having a second polarization direction. Finally, the method includes detecting changes in intensity of the light passing through the analyzer from at least two of the discrete material elements simultaneously. Changes in light intensity are the result of stress-induced birefringence of the materials in the array.

BRIEF DESCRIPTION OF THE DRAWINGS

FIG. 2b is a top view of the sample block of FIG. 2a.

FIG. 4b is a side view of the collimator block of FIG. 4a.

FIG. 7b is a side view of the temperature-controlled block of FIG. 7a.

FIG. 8b is a side view of the alternative embodiment of the temperature-controlled block of FIG. 8a.

FIGS. 22 and 23 show in-phase (E') and out-of-phase (E") components of the stress-optic shear modulus as a function of frequency for polyisobutylene samples 1 and 2 listed in Table 2.

DETAILED DESCRIPTION OF THE PREFERRED EMBODIMENT

Figure 1:
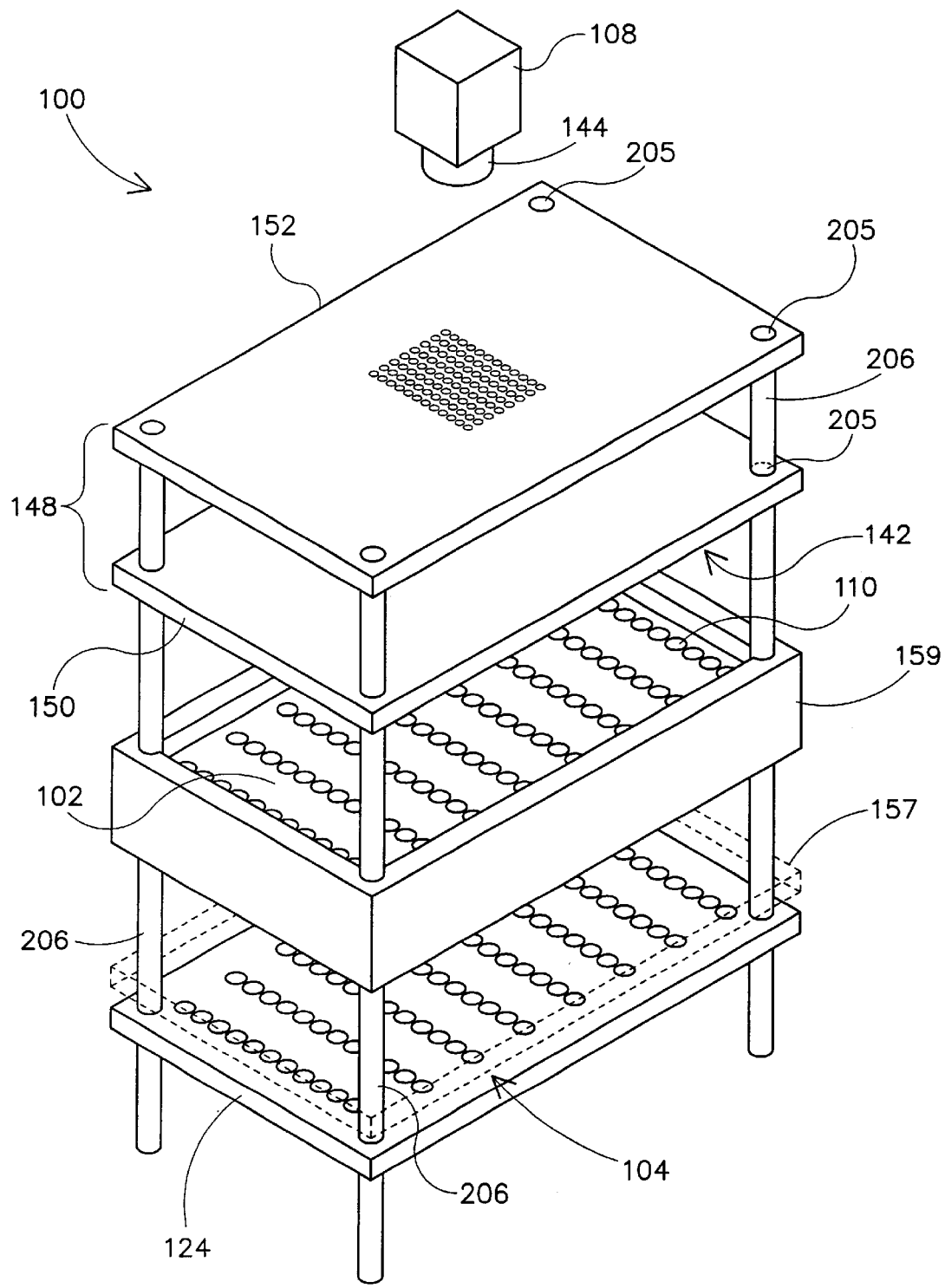
FIG. 1 is a schematic drawing of an apparatus for rapidly screening members of a combinatorial library in accordance with the present invention.

Overview of a Depolarized Light Scattering Array Apparatus

The present invention provides an apparatus and method for screening an array of material samples in a combinatorial library. Rapid screening is achieved by passing polarized light first through the compounds or materials being characterized and then through a polarizing filter, and measuring changes in the intensity of the transmitted light as a function of time and/or environmental conditions. The apparatus of the present invention allows for screening to be done simultaneously, in parallel, for two or more library material samples or to be carried out in a rapid serial manner or a combination of the two. Among other benefits, changes in the intensity of the transmitted light indicate changes in the optical characteristics of a material. The changes are generally associated with one or more structural transformations such as the melting, formation, or annealing of crystallites; the relaxation of stress-induced deformations; molecular alignment or randomization; or transitions between different crystalline or liquid crystalline arrangements of the molecules of a material. Such transformations may be driven by changes in material composition, as when volatile components of a given compound are driven off by heating above a certain temperature; by changes in environmental conditions such as temperature, pressure, or local electric field strength; or by acceleration of kinetically constrained processes such as, without limitation, the relaxation of a mechanically stressed polymer film upon heating above its glass transition temperature. Thus, the present invention may be used to monitor structural, kinetic, and thermodynamic characteristics of an array of material samples, or to identify materials desirable for a specific application.

In principle, the number of independent measurement channels available restricts the number of material samples that can be measured in parallel. This can exceed 200,000 for inexpensive, commercially available CCD cameras. However, in practice, the number of material samples is limited to the number of samples that can be prepared in a reasonable amount of time for a single set of measurements, and by the physical dimensions of the device. Typical arrays contain between 10 and 1000 samples.

In materials where the transformations or relaxations of interest are slow (e.g., polymers), the minimum measurement time is typically set by the time required for the samples to achieve equilibrium at a given set of environmental conditions (temperature, pressure, etc.) Such values generally range from 5 to greater than 15 minutes, resulting in an effective throughput in the order of 60 samples/hr for ten measurements of an array of 100 elements. In the absence of such kinetic retardation, the measurement time is frequently set by the speed at which sufficiently large environmental changes can be produced. Typical thermal ramp rates range from 0.5 to 10° C./min; measurement at 1 degree intervals yields throughputs on the order of 1200 samples/hr. Comparable performance can be obtained when varying pressure or gas composition. Although local electric and magnetic fields can be varied at much higher frequencies, measurement will be limited in practice by the speed with which samples can be prepared and loaded into the apparatus, effectively constraining the sampling rate to less that 2000 samples/hr.

To perform such measurements described above, FIG. 1 illustrates a first embodiment of an assembled depolarized light scattering apparatus 100. The apparatus 100 includes a sample block 102 for receiving material samples for a combinatorial library, a light source 104, at least one polarizer (not shown in FIG. 1) and a detector 108 for obtaining light intensity measurements. As more clearly seen in FIGS. 2a and 2b, sample block 102 includes a plurality of pre-defined regions 110 in the form of openings, illustrated by way of example as generally circular, wherein the number of regions 110 correspond to the number of material samples that may be used with apparatus 100 at one time. Regions 110 are arranged in rows 112 equally spaced apart at a predetermined distance. Each region 110 extends from a top surface 114 to a bottom surface 116 of sample block 102 so as to extend completely through sample block 102. At the top surface 114, the regions 110 have a first diameter $d_1$, while at the bottom surface 116, the regions 110 have a second diameter $d_2$, wherein diameter $d_1 > d_2$ so as to form a ledge 118. Ledge 118 serves as a support for holding the bottom surfaces of vials (not shown) containing the material samples in the combinatorial library. Preferably, the vials are transparent to light of a predetermined wavelength, to be explained further in greater detail. The vials have a diameter that is slightly smaller than first diameter $d_1$ portion, but greater than second diameter $d_2$ portion such that the vials fit securely within regions 110. Further, the length of the first diameter $d_1$ portion is substantially greater than the length of the second diameter $d_2$ portion and approximately equal to the length of vials such that the vials are fully seated within regions 110 in sample block 102, thereby minimizing temperature variations throughout the vial, as detailed below. To enable easy removal of the vials, preferably an upper portion of the vials extend slightly above top surface 114 of sample block 102. Sample block 102 is constructed of aluminum or other suitable material.

The light source 104, which provides at least one linearly polarized light beam, is positioned adjacent to the bottom surface 116 of sample block 102 such that light is directed to pass through at least one predefined region 110. Light source 104 may consist of one or more sources of unpolarized light in combination with a polarizing optical element, such as a light bulb and a sheet of polarizing film, or of a source of inherently polarized light, such as a laser or laser diode.

In one embodiment, light source 104 includes a plurality of light emitting diodes (LEDs), or other suitable light sources, such as lamps, that are adapted to simultaneously provide light beams having a narrow distribution of wavelengths. While the use of LEDs are preferred due to their low cost, low power consumption and the high intensity of the resulting light beam, it is understood that the light source 104 need not be monochromatic. The use of other suitable light sources, such as light tables or lasers, is also within the scope of this invention. However, if light source 104 only emits a single light beam and the illumination area covered by the light beam is less than the area of the array of material samples, an optical element, such as a fiber optic assembly, a combination of lenses, or a combination of lenses and mirrors must be used to divide the light beam among the material samples of the array, such that the entire array may be simultaneously illuminated.

Figure 3:
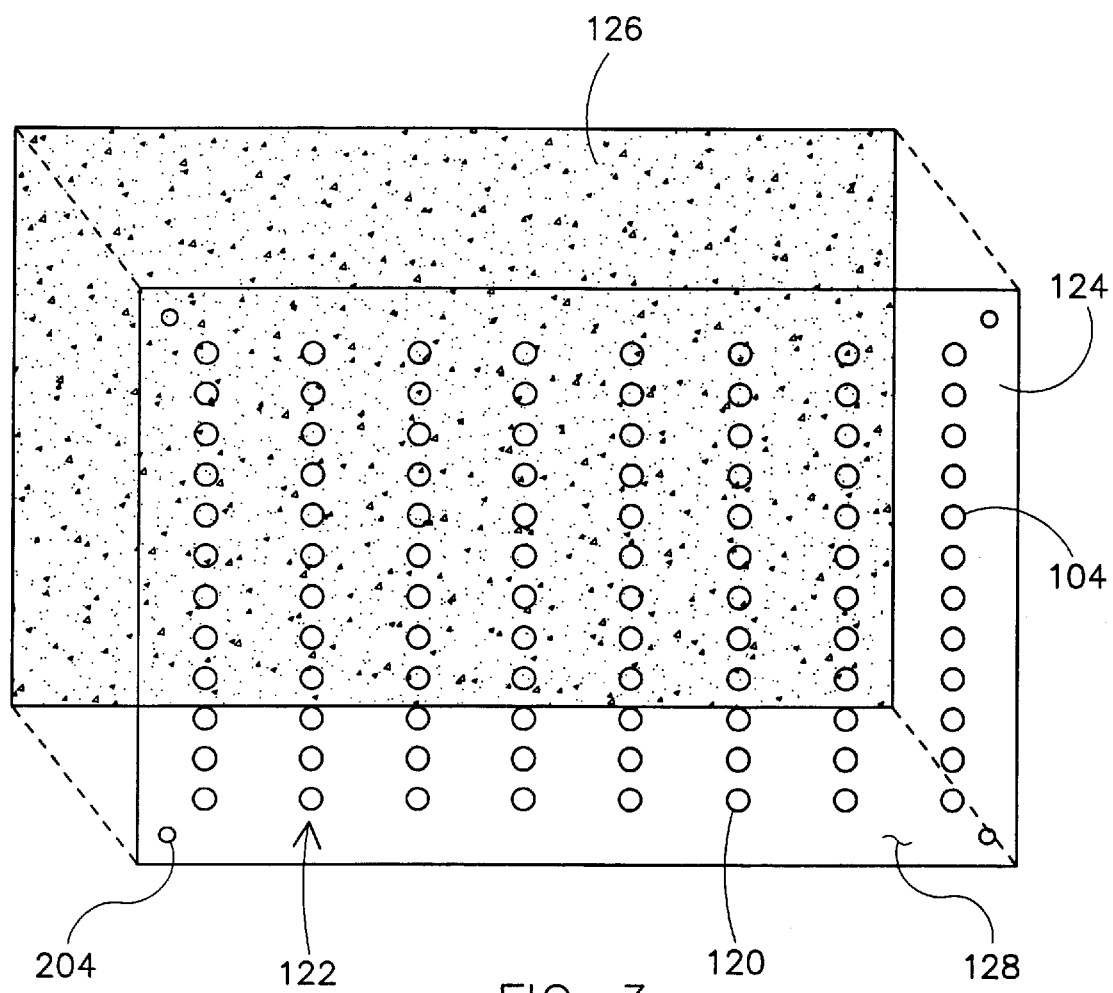
FIG. 3 is a perspective view of a light source support plate and a polarizer.

As shown in FIG. 3, the LEDs are disposed in apertures 120 along rows 122 on a support plate 124. Preferably, support plate 124 is constructed of plastic, to reduce manufacturing costs, although other suitable materials may be used. Further, support plate 124 is preferably a dark color, such as black, to reduce the occurrence of stray light scattering off support plate 124. Rows 122 correspond to rows 112 such that the LEDs are positioned so as to be substantially in alignment with regions 110, whereby the light beams are directed to pass simultaneously through the vials holding the material samples of the combinatorial library. To polarize the light beams emitted from the LEDs, a polarizing optical element ("polarizer") 126, is placed on a top surface 128 of support plate 124 containing the LEDs wherein polarizer 126 transmits only that portion of the light which has a specific linear polarization.

Alternatively, polarizer 126 may be a polarizing mirror (not shown). However, to incorporate a polarizing mirror into the apparatus, due to the angle at which the light beams must reflect from the mirror for polarization to occur (Brewster's angle), the relative positions of the light source, mirror, and sample block must be altered such that the reflected beam passes through the sample block.

Polarizer 126 polarizes the light beams before the light beams reach the vials of material samples, thus illuminating the material samples with focused linearly polarized light beams. The linearly polarized light beams have a predetermined wavelength that permits the light beams to pass through the vials and reach the material samples. As the polarized light beams are directed toward the material samples, they are partially collimated by their passage through apertures 120 of support plate 124 and apertures 110 in bottom surface 116 of sample block 102. Depending on the material samples' optical characteristics, which may be a function of factors such as composition or structure, the light beams are partially depolarized after passing through the material samples.

Figure 2A:
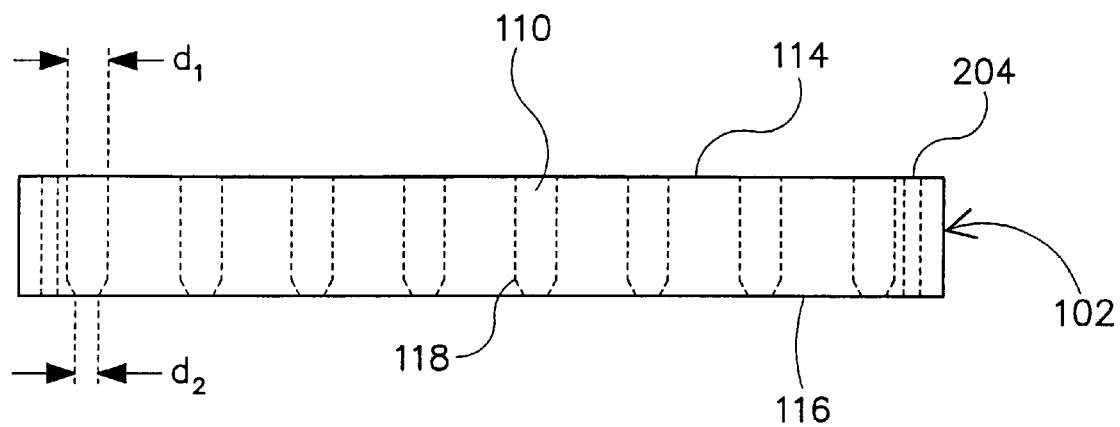
FIG. 2a is a side view of a sample block for holding the members of the combinatorial library.
Figure 2B:
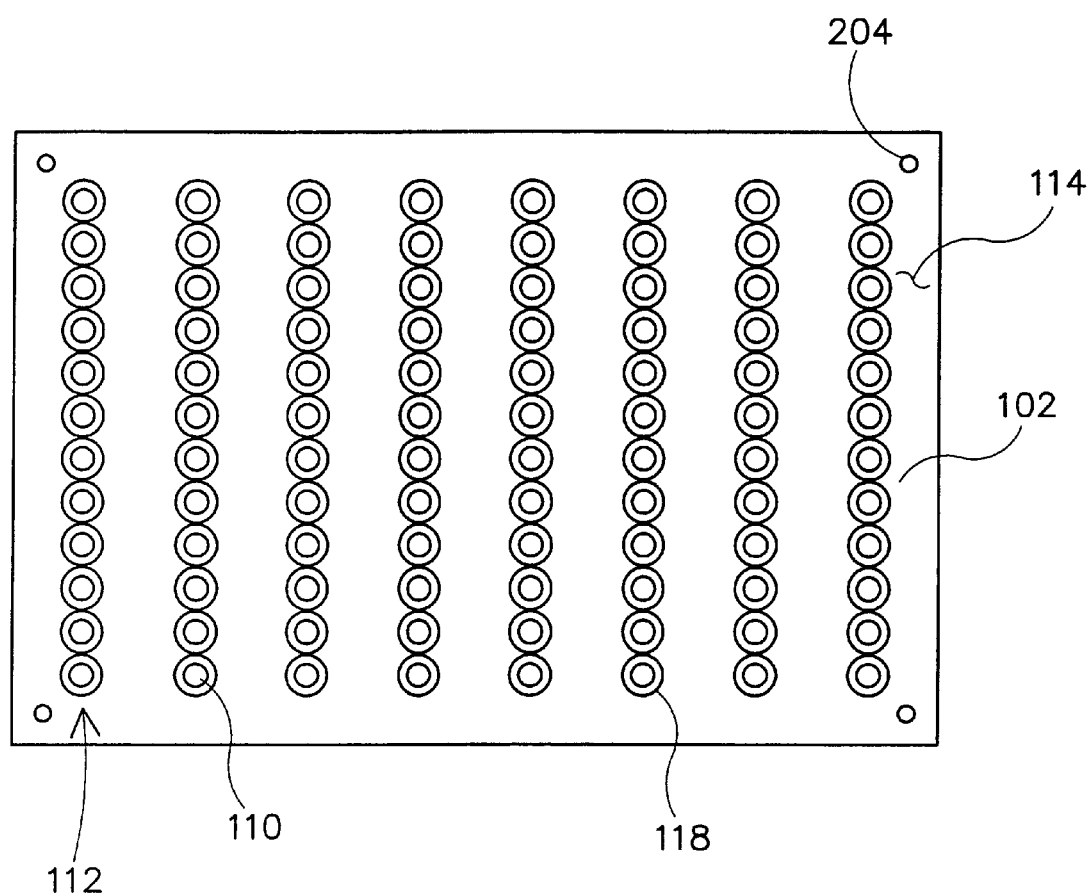

The apparatus 100 of FIG. 1 may optionally include a collimator block, that is adapted to be placed on the top surface 114 of the sample block 102, to collimate the light beams that have passed through the material samples, thereby reducing the occurrence of stray light.

Figure 4A:
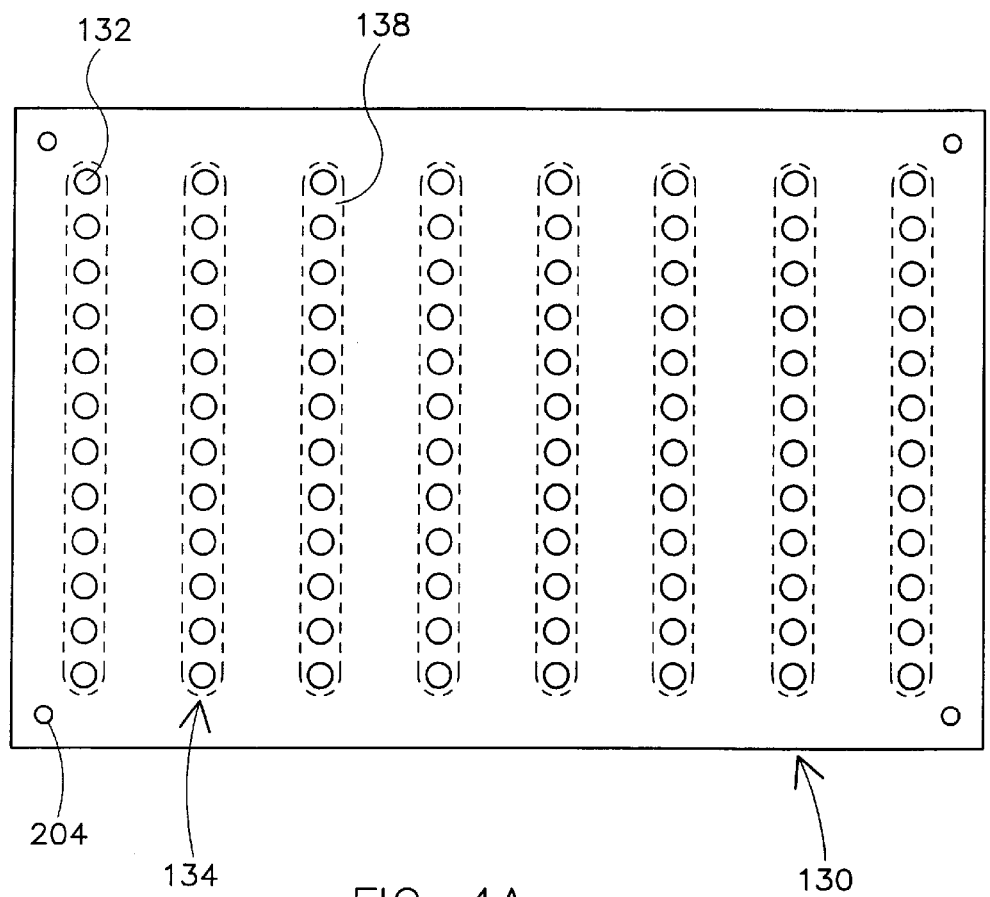
FIG. 4a is a top view of a collimator block.
Figure 4B:
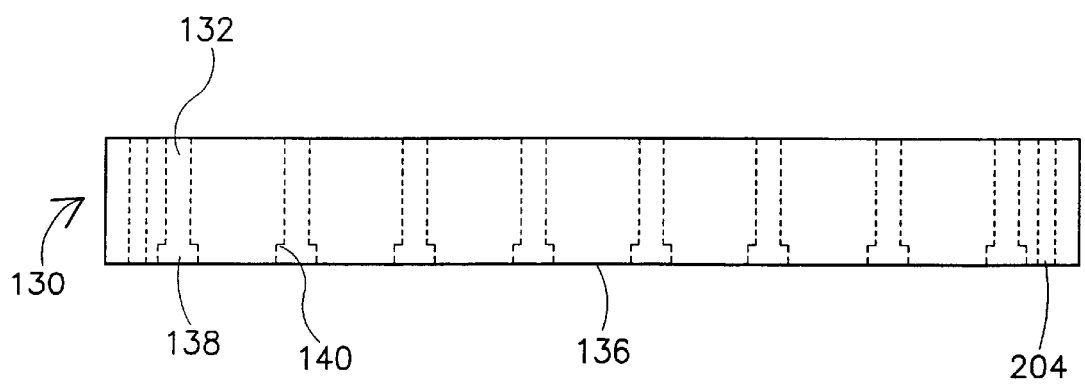

FIG. 4a and 4b show one embodiment of a collimator block 130. The collimator block 130 includes a plurality of apertures 132 arranged in rows 134 defined in the block and extending therethrough, wherein the positioning of apertures 132 correspond to positioning of regions 110. A bottom surface 136 of collimator block 130 includes a plurality of trough sections 138. Trough sections 138 are formed along each row 134 and have a width that is greater than the diameter of apertures 132. Trough sections 138 are preferred to permit the vial tops to extend into collimator block 130, such that the collimator block rests on upper surface 114 of sample block 102, as opposed to the top portion of the vials, because walls of vials that are relatively thin may break under the weight of collimator block 130. Trough sections 138 further serve to aid in properly aligning the vials and apertures 132 of collimator block 130. The differences in the width and the diameter of apertures 132 and trough sections 138 result in a lip 140. Lip 140 improves the degree of collimation.

As shown in FIG. 1, a second polarizer ("analyzer") 142, for example a commercially available linearly polarizing sheet filter, is positioned above the sample block 102 or the collimator block 130 (if present). Alternatively, a mirror may be positioned adjacent to the top surface 114 and aligned so that the light which passes through the collimator block 130 strikes the mirror surface at the polarizing angle (Brewster's angle). Preferably, the analyzer 142 is spaced away from collimator block 130, which will be explained in further detail below. The analyzer 142 serves to block out any transmitted light beams that have the same polarization direction as the incident polarized light beams originating from the light source 104, preferably allowing only depolarized light to pass through. For measurements of materials that undergo substantial changes in their optical characteristics, it is preferred that analyzer 142 has the polarization direction oriented at 90° with respect to polarizer 126, thereby, preferably resulting in complete blockage of the transmitted light if no depolarization occurs as the light beams pass through the samples. However, it is understood that apparatus 100 will still operate for other, non-zero relative orientations, such that some fraction of the incident light will be transmitted through analyzer 142 even in the absence of any depolarization.

Referring to FIG. 1, a detector 108 is positioned adjacent the analyzer 142 to capture the intensity readings from the depolarized scattered light beams and to output a signal corresponding to the intensity of the light beams as a function of time. In this manner, the intensity readings of the samples may be compared to ascertain specific desirable characteristics. Detector 108 can include one or more non-imaging optical sensors, such as semiconductor photodetectors or photomultipliers, or an imaging system such as the human eye, film or a charge-coupled device (CCD). The embodiment of FIG. 1 includes a CCD detector 108 to capture all of the intensity readings of the material samples. The CCD has a lens 144 that focuses the light as it enters detector 108. However, due to the narrow field of view of lens 144, the detector 108 must be positioned a great distance from analyzer 142 to capture the intensity readings of the material samples simultaneously. As the distance between detector 108 and analyzer 142 is increased, the sensitivity of the readings captured by detector is decreased.

Preferably, to reduce the dimensions of the region over which the light transmitted through the analyzer is distributed, detector 108 further includes an optical system such as fiber optic system 148. The fiber optic system 148 includes a first fiber optic plate 150, a second fiber optic plate 152 and fiber optic transmission media such as a plurality of fiber optic bundles (not shown). Preferably, the fiber optic plates 150, 152 are constructed of a dark plastic, preferably black, so as to be non-reflective and cost efficient to manufacture.

Figure 5:
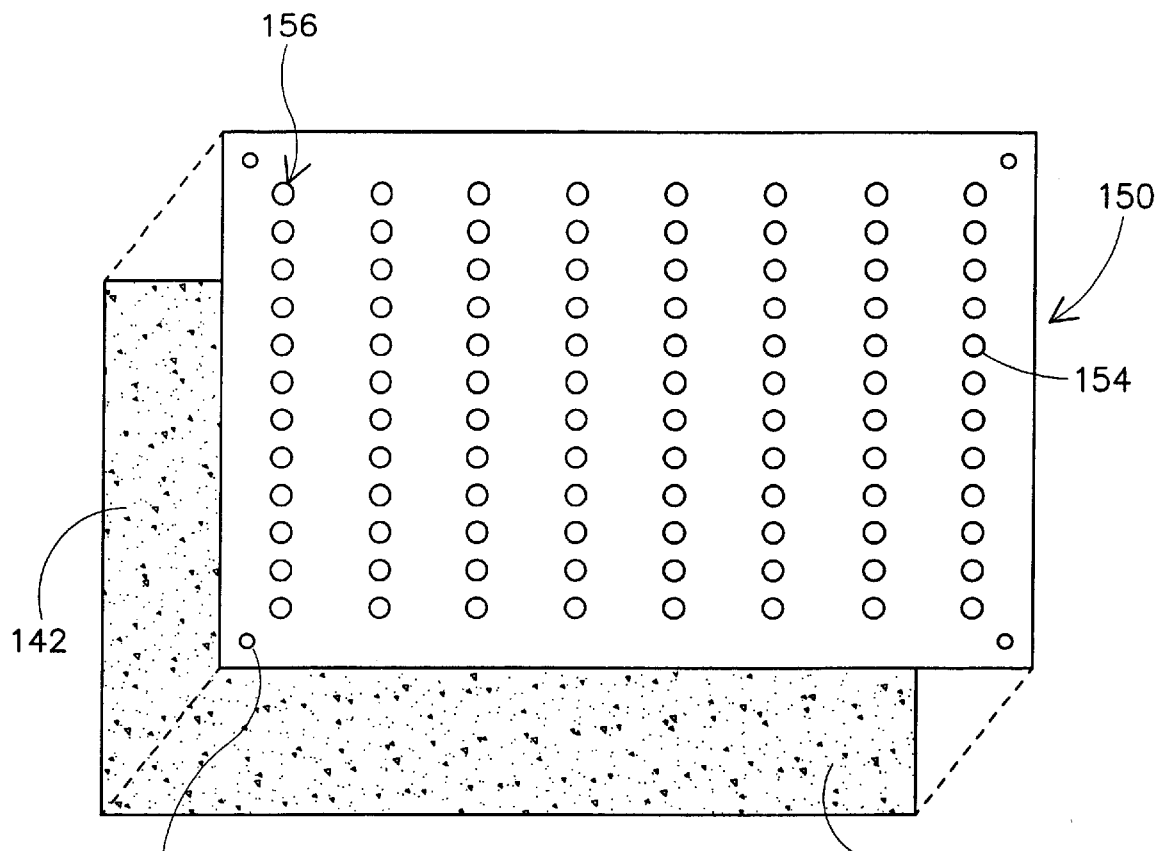
FIG. 5 is a perspective view of a first fiber optic plate and an analyzer.

As seen in FIG. 5, the first fiber optic plate 150, which is positioned on a top surface of the analyzer 142, includes an array of apertures 154 that are arranged a predetermined distance apart in rows 156 that correspond to the rows 112 of the sample block 102 (FIG. 1) such that, in operation, the vials of material samples will be in substantial alignment with the apertures 154.

Figure 6:
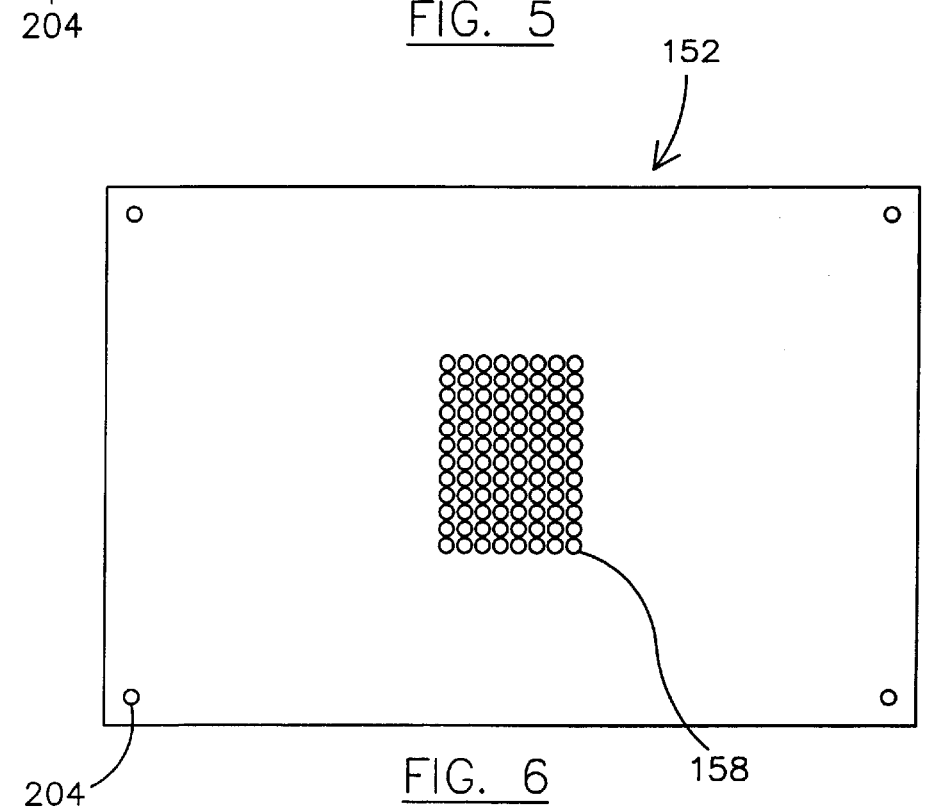
FIG. 6 is a top view of a second fiber optic plate.

The second fiber optic plate 152, as seen in FIG. 6, also includes an array of apertures 158. Apertures 158 are arranged a predetermined distance apart so as to be closely packed together such that an overall dimension of the region of apertures 158 is reduced relative to the overall dimension of the region of apertures 154 of the first fiber optic plate 150.

The plurality of fiber optic bundles (not shown) are positioned between first fiber optic plate 150 and second fiber optic plate 152. The fiber optic bundles are connected at either end to the first and second fiber optic plates 150, 152 at the respective holes 154, 156 and are in communication between first and second fiber optic plates 150 and 152. Fiber optic plates 150 and 152 cooperate with the fiber optic bundle to reduce the size of the area of transmitted light intensities, thereby enabling the detector 108 to be positioned in close proximity with the remainder of apparatus 100, while permitting simultaneous scanning and characterizing of the entire array of material samples. Alternatively, a combination of lenses or a combination of lenses and mirrors may be used.

When the apparatus 100 is used to characterize material samples that produce only weak depolarization of an initially linearly polarized light beam it is preferred that the apparatus 100 includes an optical filter 157 (shown in phantom in FIG. 1) such as a quarter-wave plate. The optical filter 157 is positioned between the polarizer 126 and sample block 102, such that the linearly polarized light beams from light source 104 must pass through optical filter 157 prior to reaching the material samples in sample block 102. The optical filter 157 preferably converts linearly polarized light into circularly polarized light. When the circularly polarized light is transmitted through the material samples and analyzer 142, the intensity of the light beam is maximally dependent upon the optical characteristics of the material sample, thereby making it possible to detect very small changes in intensity for those materials that exhibit weak depolarization characteristics.

Moreover, the use of circularly polarized light allows one to characterize optically active materials by circular dichroism measurements. Useful optical filters 157 for circular dichroism measurements include quarter wave plates or wedges, Fresnel rhombs, Pockels electrooptic modulators, photoelastic stress modulator, or similar devices for resolving plane polarized light into 1 (levorotatory) and d (dextrorotatory) components of circularly polarized light. Details concerning circular dichroism measurements are provided below.

Screening Device for Effects of Temperature

As shown in FIG. 1, the apparatus 100 may further include a temperature-controlled block 159 that is adapted to heat or cool the array of material samples to achieve a desired result. For example, the block can be adapted to heat or cool during characterization such that the detector 108 captures the intensity of the depolarized light beams and outputs a signal corresponding to the intensity of the light beams as a function of temperature, or as a function of time at a given temperature. In a preferred embodiment, the temperature-controlled block 159 is constructed of aluminum or other suitable material.

Figure 7A:
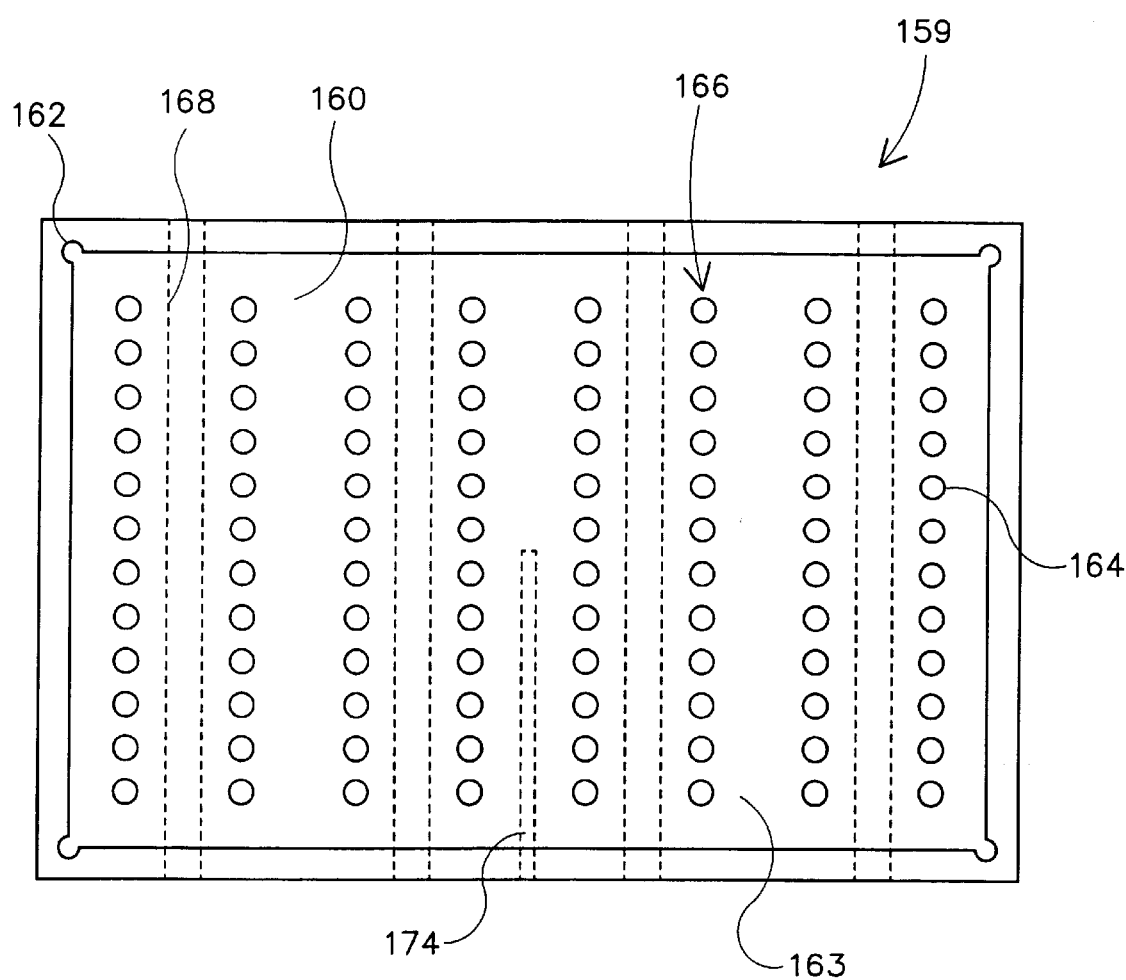
FIG. 7a is a top view of a temperature-controlled block.
Figure 7B:
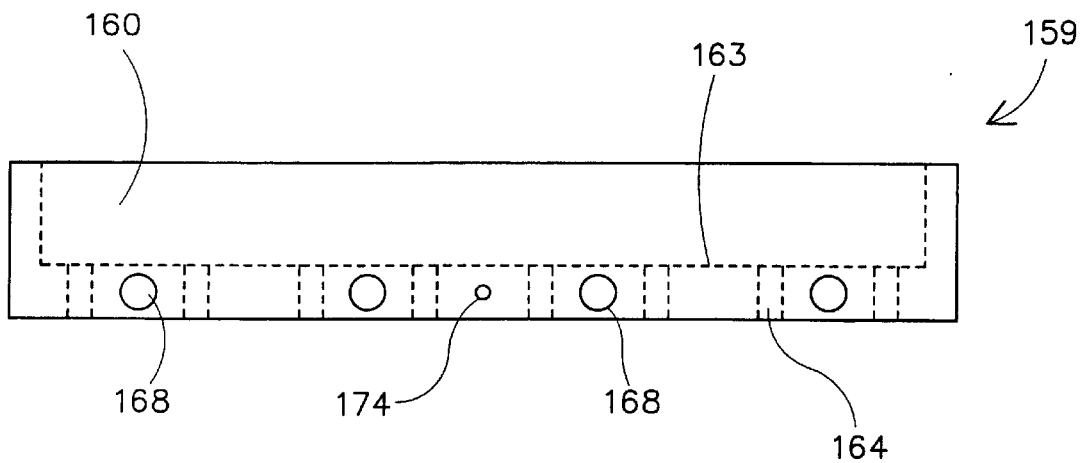

Referring to FIGS. 7a and 7b, the temperature-controlled block 159 includes a well 160 having a size and shape that corresponds to the size and shape of sample block 102 such that sample block 102 may be positioned within the well 160. Corners 162 of the well 160 are preferably radiused so as to permit easy insertion of sample block 102 within well 160.

A bottom surface 163 of the well 160 includes a plurality of apertures 164 that are arranged in rows 166, wherein the position of the apertures 164 correspond to the positions of the regions 110 in the sample block 102, such that when the sample block 102 is positioned in the well 160, the apertures 164 are in general alignment with the regions 110 in the sample block 102. The apertures 164 cooperate with the support plate apertures 120 and the regions 110 in sample block 102 to collimate the linearly polarized light beams as they pass through support plate 124, sample block 102, and the temperature controlled block 159. If aluminum, the temperature controlled block 159 is either anodized or otherwise coated in black to render it substantially non-reflective, further reducing scattered light occurrence.

In a first embodiment, the temperature-controlled block 159 includes an array of channels 168 disposed below bottom surface 163 of the well 160, between the rows 166. Channels 168 extend laterally through the temperature controlled block 159 and are adapted to receive resistance heaters or thermoelectric devices (not shown). Preferably, an external processor (not shown) controls the temperature of the resistance heaters or thermoelectric devices, although other suitable devices may be employed. The external processor monitors a signal from a monitoring device such as a thermocouple, thermistor or resistive thermal device (RTD) (not shown), positioned in a small channel 174 in approximately the center of the temperature controlled block 159. The power supplied to the resistance heaters or thermoelectric devices is adjusted in response to the signal received from the monitoring device.

Figure 8A:
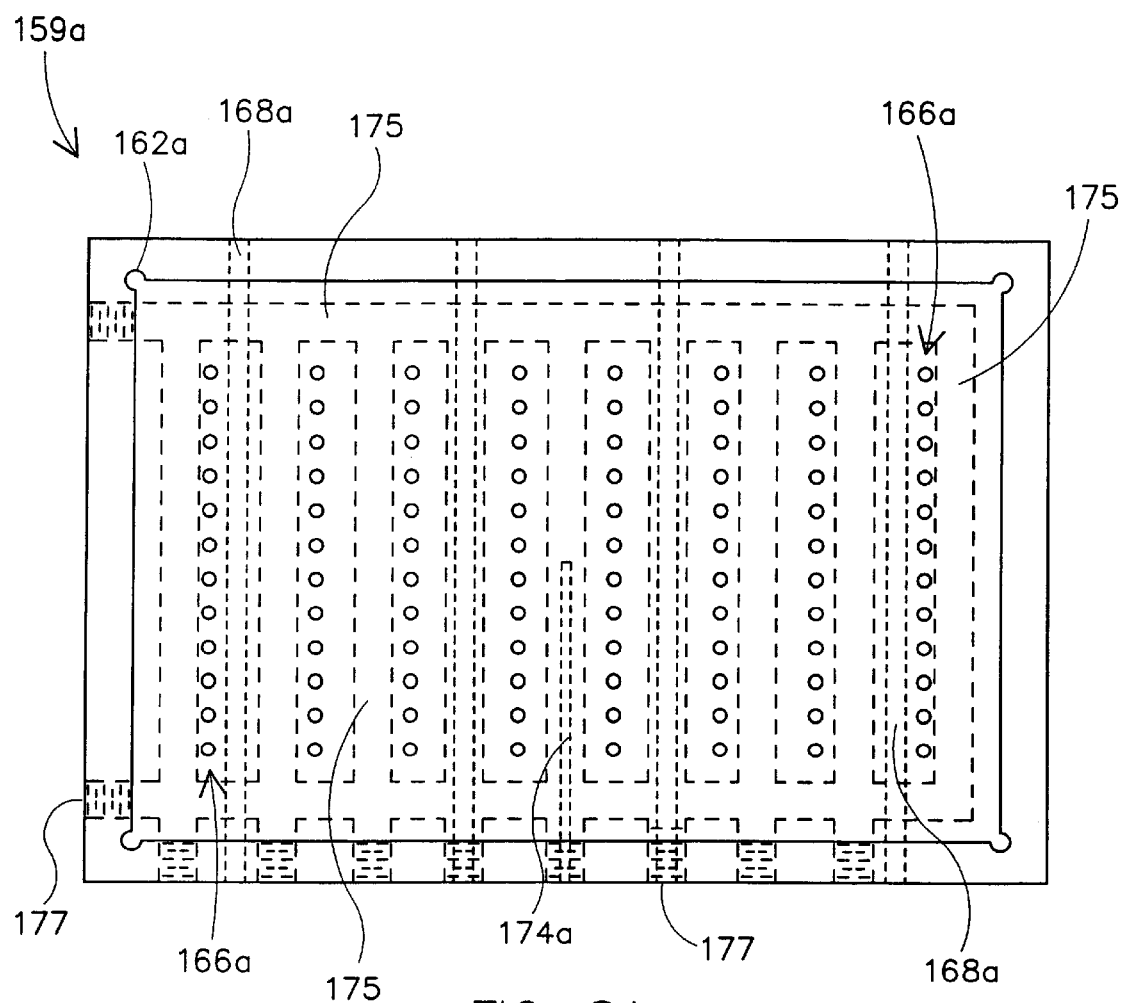
FIG. 8a is a top view of an alternative embodiment of the temperature-controlled block.
Figure 8B:
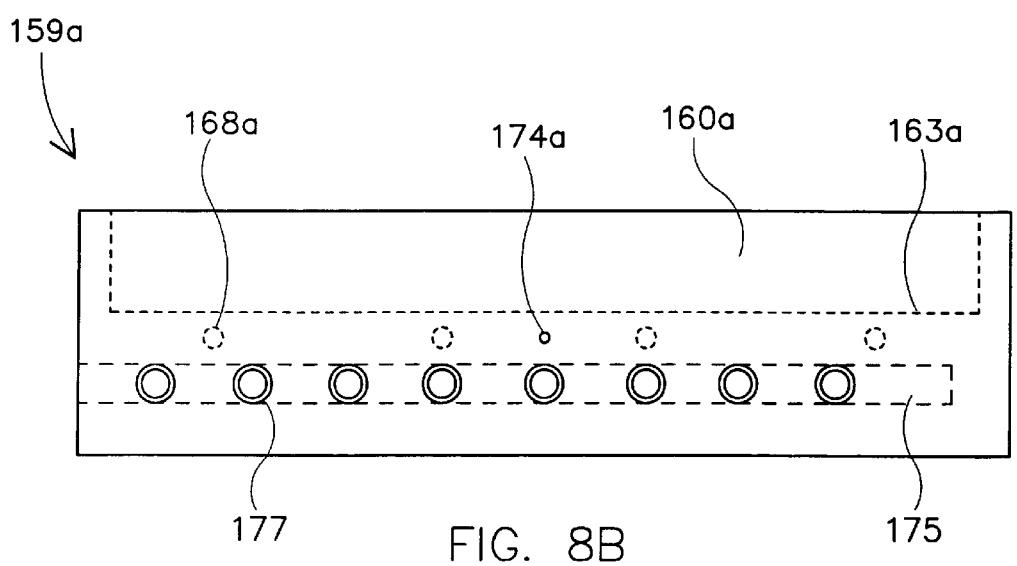

In another alternative embodiment, referring to FIGS. 8a and 8b, a temperature-controlled block 159a may include both passages 175 carrying temperature agents and either channels 168a for resistance heaters or thermoelectric devices mounted to a surface of the temperature controlled block 159a. The temperature agents and resistance heaters or thermoelectric devices work together to vary the temperature of the temperature-controlled block 159a. Similar to the channels 168 of the embodiment shown in FIG. 7a and FIG. 7b, the passages 175 are disposed below the bottom surface 163a of the well 160a and between the rows 166a. However, the passages 175 are adapted to receive a liquid temperature agent (not shown) to vary the temperature of temperature controlled block 159a. Suitable temperature agents (which may be heated or cooled) include water, silicone oil or fluorinated solvent. Other suitable temperature agents may also be employed. In one embodiment, to ensure proper temperature control of the temperature controlled block 159a, the passages 175 extend both in a lateral and horizontal direction so as to extend around the perimeter of block 159a and between rows 166a. Entrance and exit ports 177 of the passages 175 are preferably threaded so as to permit easy assembly of tubing to a separate temperature agent reservoir.

In another embodiment, the temperature controlled block 159a may include both channels 168a for resistance heaters and passages 175 carrying temperature agents working in combination to vary the temperature of temperature controlled block 159.

Screening Device for Effects of Pressure and Environment Composition

Figure 9:
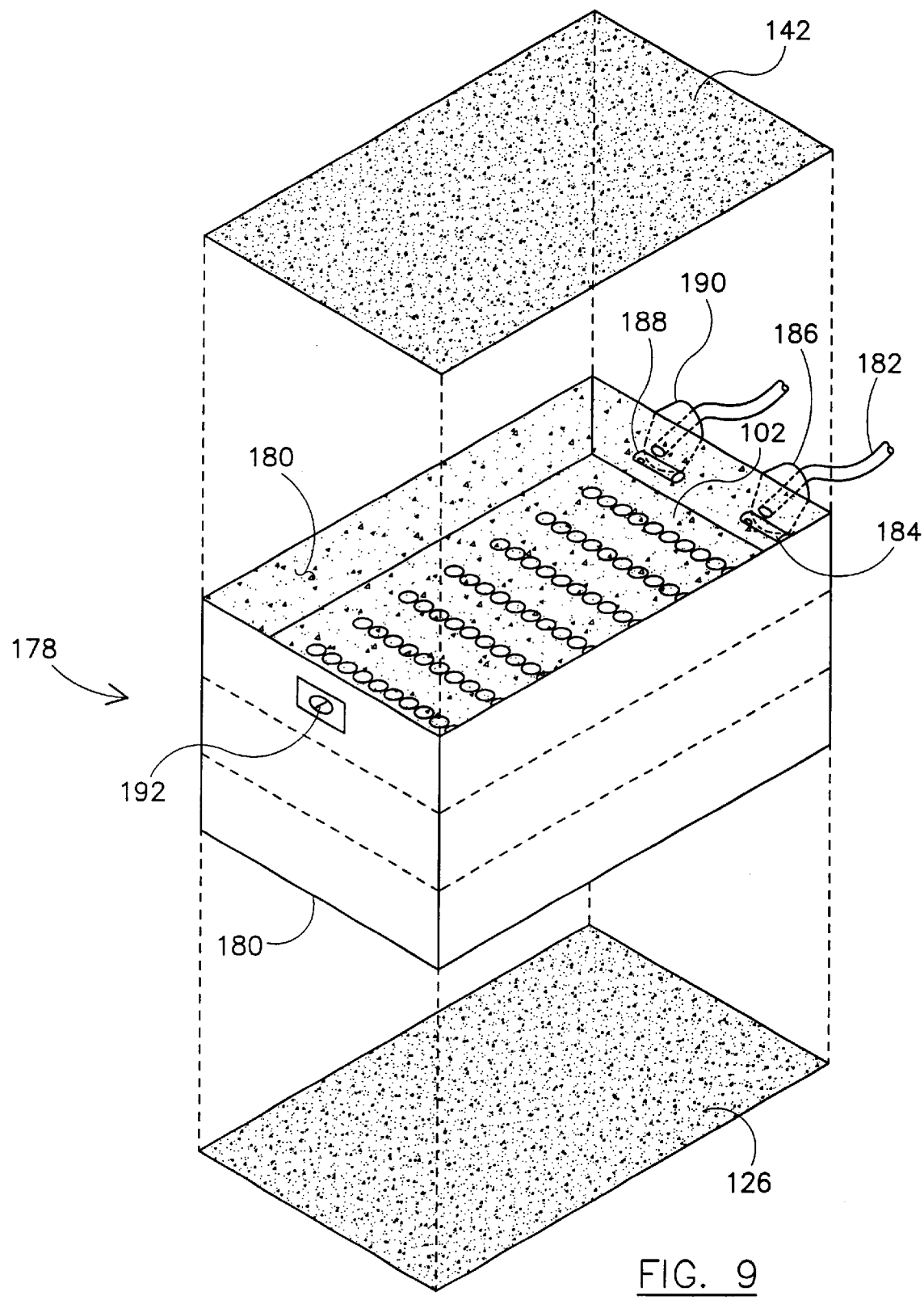
FIG. 9 is a schematic drawing of a substantially gas-tight environmental chamber with the sample block mounted therein.

Referring to FIG. 9, the apparatus 100 may include at least one environmental chamber 178, preferably gas tight, positioned between the polarizer 126 and the analyzer 142. The sample block 102 is mounted within the chamber 178. Both the upper and lower surfaces of the chamber 178 are provided with optically transparent windows 180 that permit the light beams to reach the material samples within the sample block 102 and to pass through to the analyzer 142. At least one gas, which is directed into chamber 178 through a conduit 182 or other suitable passageway pressurizes the chamber 178. A pressure sensor 184 working in combination with an external processor (not shown) operates a servomechanically actuated regulator valve 186 or piston to control the pressure of the substantially gas-tight environmental chamber 178. The detector 108 (FIG. 1) captures the depolarization data and outputs a signal corresponding to the data as a function of pressure, or of time at a given pressure.

In another embodiment, the chamber 178 is continuously filled with a mixture of two or more gases. In this embodiment, additional conduits 188 and servomechanically actuated regulator valves 190 are provided to control the flow of the gases into the chamber 178. An external processor (not shown) serves to operate the regulator valves 190. Alternatively, the gases may be mixed in a separate chamber (not shown), wherein the amounts of each gas being directed into the chamber is controlled by separate regulator valves. Once the gases are mixed they are then transported from the separate chamber via the conduit 182 into the chamber 178. A calibrated vent valve 192 is also included on chamber 178 to continuously permit a predetermined amount of the mixture to be vented from the chamber 178. The detector 108, positioned on the top of the analyzer 142, captures depolarization data generated from the light beams passing through the material samples and the analyzer and outputs a signal corresponding to the data as a function of gas composition, or of time at a specific gas composition.

In another embodiment, the sample block 102 may be subdivided into a plurality of sealed zones (not shown), wherein each zone has at least one material sample disposed therein. Each zone would receive a separate gas or gas mixture and would experience a different pressure. Alternatively, each material sample may be sealed in a transparent vessel (not shown) wherein the pressure inside each vessel is changed by varying the temperature of the vessel.

Screening Device for Effects of Electric Fields

Figure 10:
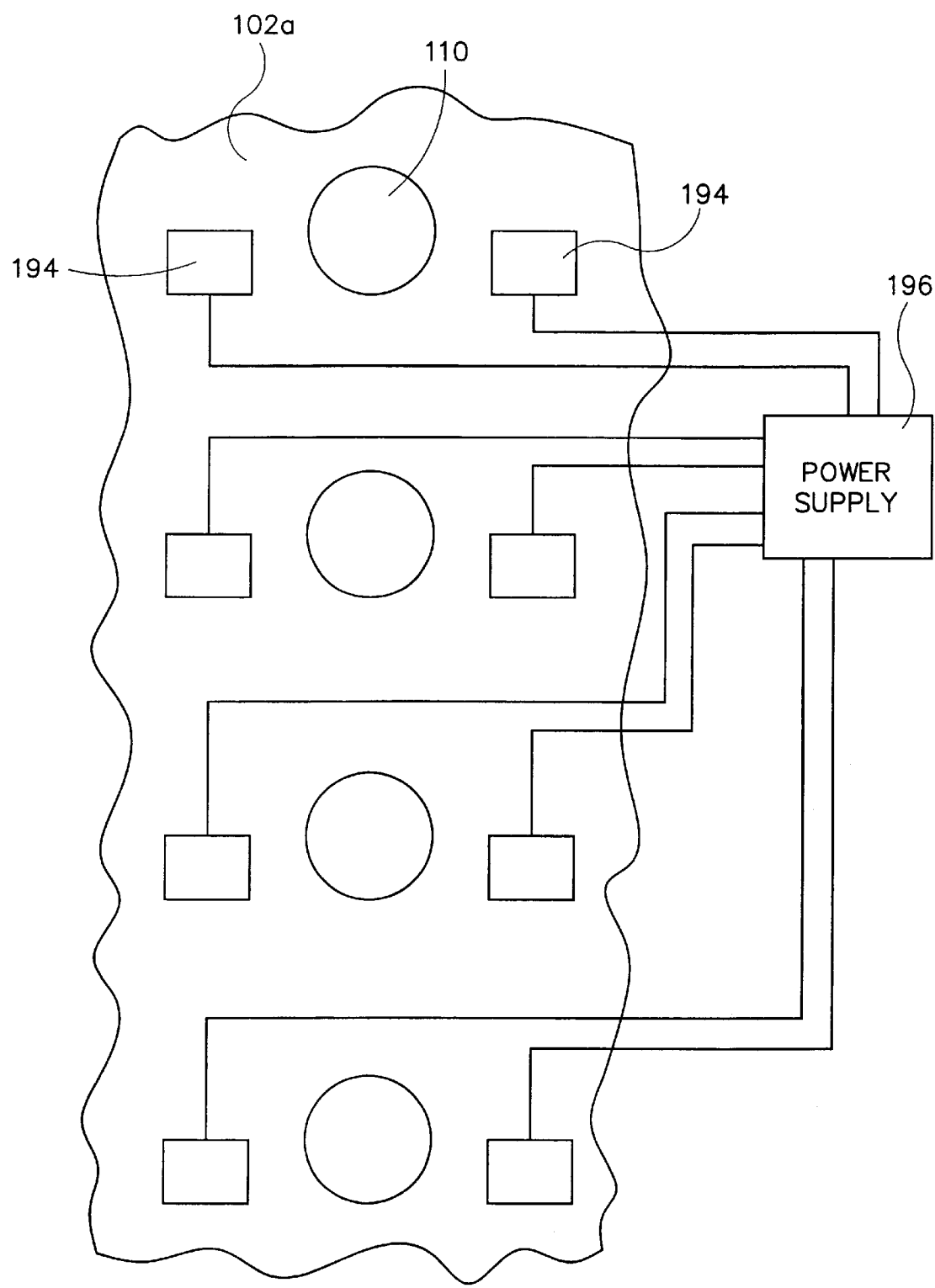
FIG. 10 is a cutaway of an alternative embodiment of the sample block having electrode pairs embedded therein.

FIG. 10 shows a cut-away portion of a sample block 102a, where the sample block 102a includes pairs of electrodes 194 embedded therein. Each pair of electrodes 194 are arranged in an opposing manner with a single region 110 positioned there between. The electrodes 194 are connected in parallel to a power supply 196, such that application of voltage across the pairs generates an electric field across each material sample. The electric field orients molecules or supramolecular assemblies within the material sample, thereby producing a change in the depolarization characteristics of the material samples. The detector 108 captures depolarization data of the material samples and outputs a signal corresponding to the data as a function of electric field strength, as a function of time after the electric field is applied or removed, or as a function of the frequency of an alternating electric field.

When scanning the material samples as a function of voltage, preferably the sample block is a planar sheet of glass 102a upon which material samples are deposited. An array of electrode pairs is arranged on the glass 102a to permit generation of high electric fields at only modest levels of applied voltage.

Screening Device for Effects of Magnetic Fields

Figure 11A:
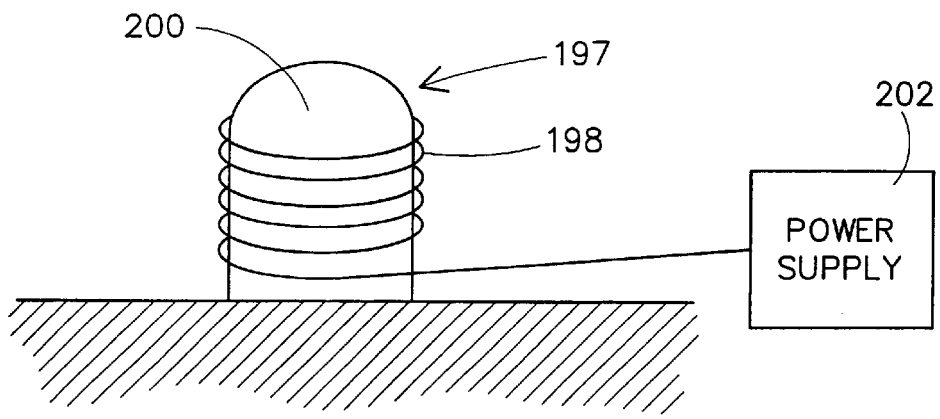
FIG. 11a is a schematic drawing of a solenoid device.
Figure 11B:
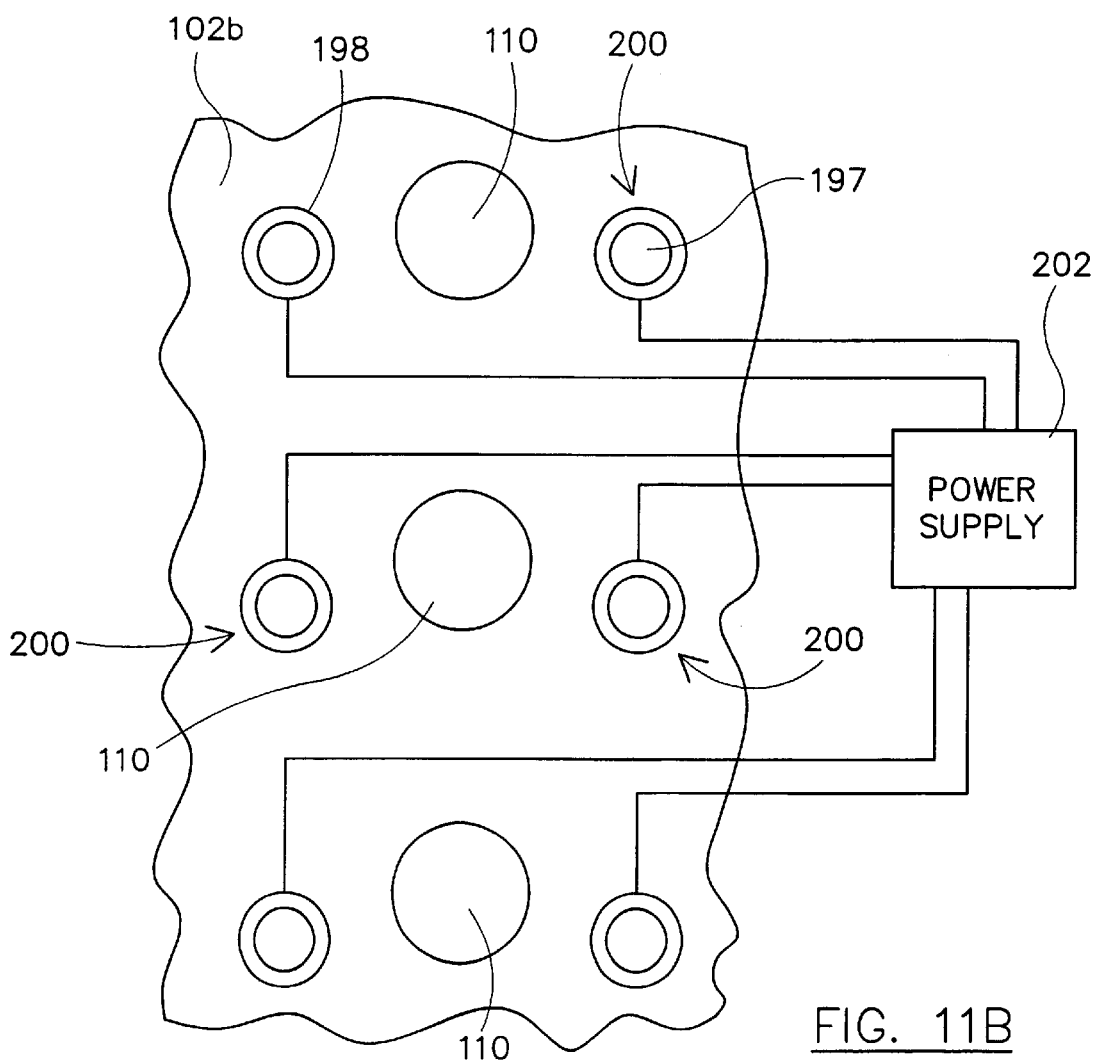
FIG. 11b is a cutaway of another embodiment of the sample block with pairs of the solenoid devices of FIG. 11 incorporated therein.

FIGS. 11a and 11b show a sample block 102b that includes a means of generating a magnetic field that surrounds each sample. In the preferred embodiment, the sample block 102b includes pairs of solenoids 197. The solenoids 197 are electromagnetic devices that generate a strong magnetic field when an electric current passes through them. As shown in FIG. 11a, the solenoids 197 typically include a wire coil 198 wrapped around a solid core 200 made of a material having a high magnetic susceptibility, such as soft iron.

Referring to FIG. 11b, each solenoid pair 197 is arranged in an opposing manner with a single region 110 receiving a vial containing a material sample positioned there between. The solenoids 197 are connected in parallel to a power supply 202, such that application of an electric current across the pairs generate a magnetic field across each material sample. The magnetic field couples to the magnetic moment of molecules or supramolecular assemblies within the material sample, thereby orienting them with respect to the field and producing a change in the depolarizing characteristics of the material sample. The detector 108 (FIG. 1) captures depolarization data of the material samples and outputs a signal corresponding to the data as a function of magnetic field strength, as a function of time after the magnetic field is applied or removed, or as a function of the frequency of an alternating magnetic field.

Figure 12:
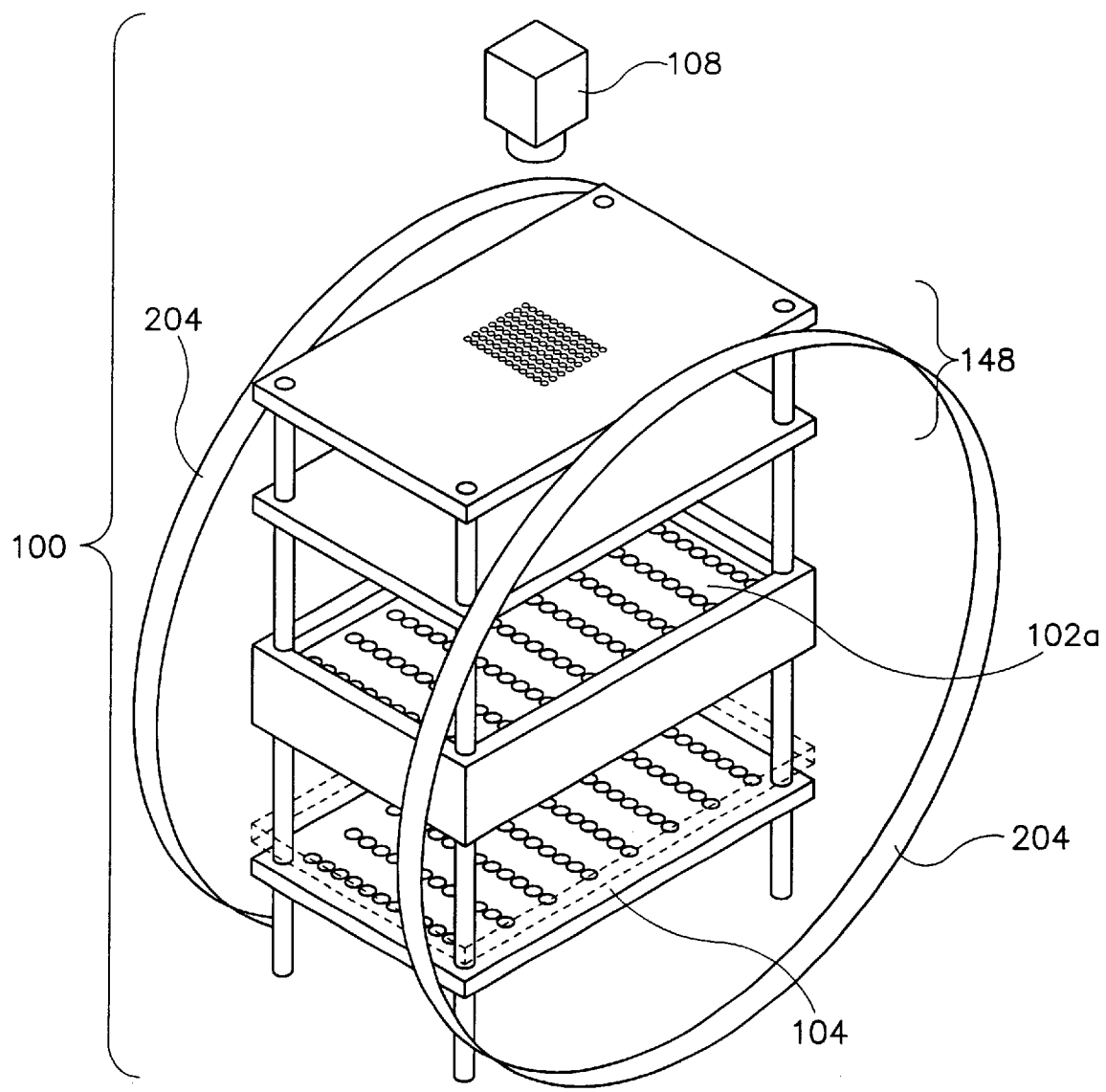
FIG. 12 is a schematic drawing of another embodiment of the apparatus incorporating a pair of circular wire coils.

As shown in FIG. 12, the magnetic field may be generated by surrounding the light source 104, the polarizer 126, the sample block 102b, the analyzer 142 and the fiber optic system 148 with a pair of circular wire coils 204 (i.e., Helmholz coils), through which a current is passed. The wire coils 204 generate a relatively weak but spatially uniform magnetic field over the entire apparatus 100. In cases where it is desired to generate an extremely high magnetic field strength, the apparatus 100 may be surrounded by one or more electromagnets (not shown). However, in both of these embodiments, the sample block must be constructed of a nonmagnetic material. Preferably, both materials should be made from non-conducting materials in order to facilitate measurements with alternating magnetic fields.

Assembly of Depolarized Scattering Light Array

Apparatus 100 is assembled so as to have all of the components arranged in series. As such, the support plate 124, the collimator block 130, the first fiber optic plate 150 and the second fiber optic plate 152 are all provided with connector holes 205 at their respective corners that are adapted to receive connector rods 206, as shown in FIG. 1. Starting with the bottom, apparatus 100 is assembled such that the support plate 124 supporting the light source 104 is in the first position with the light source 104 simultaneously emitting a plurality of light beams upwardly in a linear direction to simultaneously illuminate the entire array of material samples. The polarizer 106 is placed on a top surface 128 of the support plate 124 to polarize the emitted light beams from the light source 104.

The sample block 102, 102a or 102b, holding vials of material samples to be characterized in the regions 110, is positioned above and in the path of the light beams emitted by the light source 104 such that the polarized light beams are directed to pass through the material samples. The sample block 102 may be disposed in well 160 of the temperature-controlled block 159 and mounted in the environmental chamber 178. Alternatively, the sample block 102a or 102b is positioned alone above the polarizer 106. In the preferred embodiment, the sample block 102 is either anodized, if aluminum, or has a black outer surface to render it substantially non-reflective, thereby reducing scattered light occurrence. Next, the collimator block 130 is placed on the top surface 114 of the sample block 102 to collimate the polarized light beams that are directed through the array of material samples. In one embodiment, the collimator block 130 is constructed of polytetrafluoroethylene (e.g., TEFLON™), and painted black to reduced stray light from scattering inside the collimator block 130. TEFLON™ is preferred for its high melting temperature, thereby enabling the collimator block 130 to rest directly on a heated sample block 102. Further, TEFLON™ is a poor thermal conductor, thereby keeping analyzer 142 from melting. Other plastics having similar characteristics, such as polyimide (e.g., without limitation, KAPTON™), may be employed in a similar manner.

The analyzer 142, having a polarizing direction oriented, in one embodiment, at 90° to filter out any transmitted light that has the same polarization direction as the incident light beams, is placed above the collimator block 130. Preferably the analyzer 142 is spaced away from collimator block 130 a predetermined distance so as to produce an air gap between the collimator block 130 and the analyzer 142 when the temperature controlled block 159 is used to heat the sample block 102, as the heat would soften analyzer 142, causing loss of polarizing ability. The air gap may also serve as additional thermal insulation.

Next, a first fiber optic plate 150 is placed on a top surface of the analyzer 142 and a second fiber optic plate 152 is placed spaced apart from and above first the fiber optic plate 150. A plurality of fiber optic bundles are arranged in a tapered configuration between the first fiber optic plate 150 and the second fiber optic plate 152 to reduce the dimension of the area of transmitted light intensities. A detector 108, such as a CCD camera, is placed above the second fiber optic plate 152 to simultaneously capture intensity readings from the entire array of material samples. Preferably, the detector 108 is in communication with a data storage device (not shown) to permit analysis of the intensity readings.

Depolarized Scattering Method for Characterizing an Array of Materials

To screen and characterize the array of material samples, the material samples are provided in vials in regions 110 on a sample block 102, 102a or are placed on a top surface of a sample block 102b at regions 110. At least one material sample of the array is illuminated with a linearly polarized light beam having a predetermined wavelength. The vials or the sample block 102b itself are transparent to the predetermined wavelength of the light beam such that the light beam is permitted to pass through to the material sample. The light beam is modified after it passes through the material sample by passing the polarized light through an analyzer 142 that has a polarizing direction preferably oriented at 90° with respect to the polarizing direction of the linearly polarized light beam so as to completely filter out light intensities having the same polarization direction as the incident light beam. Next, changes in the intensity of the light beam due to changes in the optical characteristics of the material samples are detected and characteristics of the material sample are determined based on the intensity readings as a function of time.

In a preferred method, the step of illuminating the material sample includes providing a light source 104 that comprises a plurality of LEDs that simultaneously emit a plurality of light beams which are passed through a polarizer 126 so as to produce linearly polarized light beams. The linearly polarized light beams simultaneously illuminate the entire array of material samples. After the polarized light beams pass through the array, the beams are then collimated prior to being directed through the analyzer 142.

In an alternative method, the light beams are converted to circularly polarized light by passing the linearly polarized light beams through an optical filter 157 prior to reaching to material samples. The circularly polarized light permits scanning and characterizing of material samples that produce weakly polarized light beam intensities when subjected to linearly polarized light beams.

The detecting and determining step of the method includes collecting readings of the changes of light intensity of the light beams that pass through the array of material samples. After the intensity of the polarized light beams are filtered by the analyzer 142, the changes in intensity values are passed through a first fiber optic plate 150. Fiber optic bundles extending from the first fiber optic plate 150 are connected to a second fiber optic plate 152 in a tapered configuration to reduce the area of transmitted light intensities such that intensity readings of the material samples may be captured simultaneously. A CCD camera is then provided to capture the intensity readings at predetermined time intervals, wherein the intensity readings provide information on the characteristics of the array of materials.

The method may further include the step of varying the temperature of the array of material samples at a predefined rate. This step is accomplished by placing a sample block 102 into the temperature-controlled block 159. As such, the determining step may be performed as a function of temperature or, alternatively, the material samples are heated or cooled to a fixed temperature and the changes in intensity are detected as a function of time.

In addition, the method may include subjecting the material samples to pressure by enclosing the material sample in a environmental chamber 178 and a filling chamber 178 with at least one gas. As such, the determining step may be performed as a function of pressure.

The method may further include continuously subjecting the material sample to a mixture of two or more gases. This step is accomplished by enclosing the material sample within the environmental chamber 178 and continuously filling the chamber 178 with the mixture of two or more gases. The mixture is vented from the chamber 178 at a predetermined rate. The determining step may be performed as a function of gas composition.

The method may also include the step of generating an electric field across each material sample. The electric field orients the molecules of the material samples or any supramolecular assemblies within the material samples, thereby changing the depolarization structure of the material samples. The determining step is then able to be performed as a function of electric field strength, as a function of time after the electric field is applied or removed, or as a function of the frequency of an alternating electric field.

Furthermore, the method may include the step of generating a magnetic field across each material sample. The magnetic field couples to the magnetic moment of the molecules or the supramolecular assemblies within the material sample, thereby orientating the molecules or assemblies with respect to the magnetic field and producing a change in the depolarizing characteristics of the material sample. The determining step is then able to be performed as a function of magnetic field strength.

Circular Dichroism Measurements

As noted above, circular dichroism measurements can be used to characterize materials. Circular dichroism, like optical rotary dispersion, is based on interactions between circularly polarized light and optically active materials. Whereas optical rotary dispersion measures the wavelength dependence of the molecular rotation of the material, circular dichroism measures differences in molar absorptivity $(\epsilon_l-\epsilon_d)$ following illumination with l or d circularly polarized light. The difference in molar absorptivity can be positive or negative and converts plane polarized radiation to an elliptically polarized beam in which the ratio of the minor axis to the major axis of the elliptical beam path is given by $\tan^{-1}\theta$, where $\theta$ is the ellipticity. The ellipticity is approximated by $$\theta = \frac{1}{4}(k_l - k_d),\qquad\text{I}$$

where $k_l$ and $k_d$ are the absorption coefficients of the circularly polarized l and d radiation and $\theta$ is expressed in radians. The quantity $(k_l-k_d)$ is called the circular dichroism. The molecular ellipticity $[\theta]$, which has units degree-cm$^2$ per decimole, is given by the expression $$[\theta]=3305(\epsilon_l-\epsilon_d).\qquad\text{II}$$

Using Beer's law, equation II can be written in terms of light intensity (for a single beam measurement):

$$[\theta] = \frac{3305}{bc}\log\frac{I_d}{I_l}\qquad\text{III}$$

In expression III, I is the intensity (power) of the circularly polarized light after having passed through a solution of length b and containing a molar concentration c of the sample.

Circular dichroism measurements can be carried out in a manner similar to the methods discussed above. The material samples are provided in vials in regions 110 on a sample block 102, 102a or are placed on a top surface of a sample block 102b at regions 110. An optical filter 157, such as a quarter wave plate, is placed between the material samples and a source of plane polarized light. With the optical filter 157 set to produce d circular rotation, at least one material sample of the array is illuminated with circularly polarized light having a predetermined wavelength. From the sample, the light passes through the analyzer 142 having a polarizing direction preferably oriented at 90° to the polarizing direction of the linearly polarized light so as to filter out completely light intensities having the same polarization direction as the incident light beam. If the sample is optically active, it rotates the light, which changes the light intensity monitored at the detector 108. The illumination and detection steps are repeated for the l component of the circularly polarized light by, for example, rotating the quarter wave plate 90°. The molecular ellipticity can be calculated from expression III.

Preferably, the step of illuminating the material sample includes providing a light source 104 that comprises a plurality of LEDs that simultaneously emit a plurality of light beams which pass through a polarizer 126 so as to produce linearly polarized light beams. Next, the linearly polarized light passes through an optical filter that resolves the light into l or d components of circularly polarized light, which simultaneously illuminate the entire array of material samples. After the circularly polarized light beams pass through the array, they are typically collimated prior passing through the analyzer 142.

The detecting and determining step of the method includes collecting readings of the changes of light intensity of the light beams that pass through the array of material samples. After the analyzer 142 filters the polarized light beams, the light typically passes through a first fiber optic plate 150. Fiber optic bundles extending from the first fiber optic plate 150 are connected to a second fiber optic plate 152 in a tapered configuration to reduce the area of transmitted light intensities such that intensity readings of the material samples may be captured simultaneously. The method provides a CCD camera or other detector 108 to capture the intensity readings at predetermined time intervals. As noted above, the method may include varying the temperature, pressure, ambient gas composition, electric field strength or magnetic field strength of the samples.

Monitoring Birefringence and Relaxation Behavior of Materials Subject to Shear Stress: A Parallel Rheo-Optical Indexer Generally, the disclosed depolarized light scattering array measures, for each element of a material array, anisotropy in refractive index as a function of an applied scalar or vector field. As discussed above, anisotropy can result from structural transitions induced by changes in temperature, pressure, or chemical composition of the surroundings, or by structural alignment induced by subjecting the material array to electric or magnetic fields. Anisotropy can also result from mechanically deforming a material, which can affect, for example, segmental orientations in polymer samples, orientation of surface micelles, concentration and orientation fluctuations of colloidal dispersions, and unit cell dimensions of crystalline materials.

Thus, suitably modified, the depolarized light scattering array of FIG. 1 can be used to monitor stress-induced birefringence and relaxation behavior of an array of complex materials that include polymer melts, polymer blends, polymer solutions, surfactant solutions, and colloidal dispersions. During deformation, the mechanically induced structural distortion of the material results in a measurable birefringence that, for many materials, is proportional to the stress in the material. For example, in polymer systems, the proportionality is known as the "stress-optic rule" and the field that probes the relationship between stress and birefringence is known as "rheooptics." Since the strain is known, one can qualitatively determine the relationship between stress and strain as a function of system variables, including temperature, pressure, strain amplitude, strain rate, composition, electric field amplitude, and magnetic field amplitude—provided the material obeys the stress-optic relation. If the coefficient of proportionality between the stress and the birefringence, ("stress-optic coefficient") is known, these relationships can be quantified. In certain cases, a relationship can be extracted from the data even if the material does not obey the stress-optic relation as long as certain assumptions are made regarding the distribution of stresses within the material and the resulting molecular deformations. This technique can be applied to any material that transmits polarized light of the appropriate wavelength and exhibits stress-induced birefringence.

Instruments that are used to measure stress-induced birefringence in material samples are commonly called rheo-optical indexers. Such instruments are typically employed as "mechanical spectrometers," in which a material sample is subject to a sinusoidally varying strain at a selected frequency. For small strain amplitudes, the oscillatory straining results in a sinusoidally varying shear stress at the same frequency of the straining, although the stress and strain are generally out of phase. The resulting deformation modulus—i.e., stress divided by strain—is interpreted in terms of an in-phase part (storage modulus), which represents elastic deformation of the material, and an out-of-phase part (loss modulus), which represents the degree of mechanical loss.

Although researchers have used rheo-optic indexers to study mechanical properties of materials, existing rheo-optic indexers measure stress-induced birefringence one sample at a time, making them unsuitable for screening or characterizing combinatorial arrays. When used as mechanical spectrometers, rheo-optic indexers must accurately measure the phase shift between stress and strain waveforms, which requires measuring both waveforms over many cycles (at least ten). Since the frequencies involved are typically in the range of about 0.01 to about 10 Hz, the minimum measurement time is quite long and generally limits the throughput and usefulness of conventional indexers.

Figure 13:
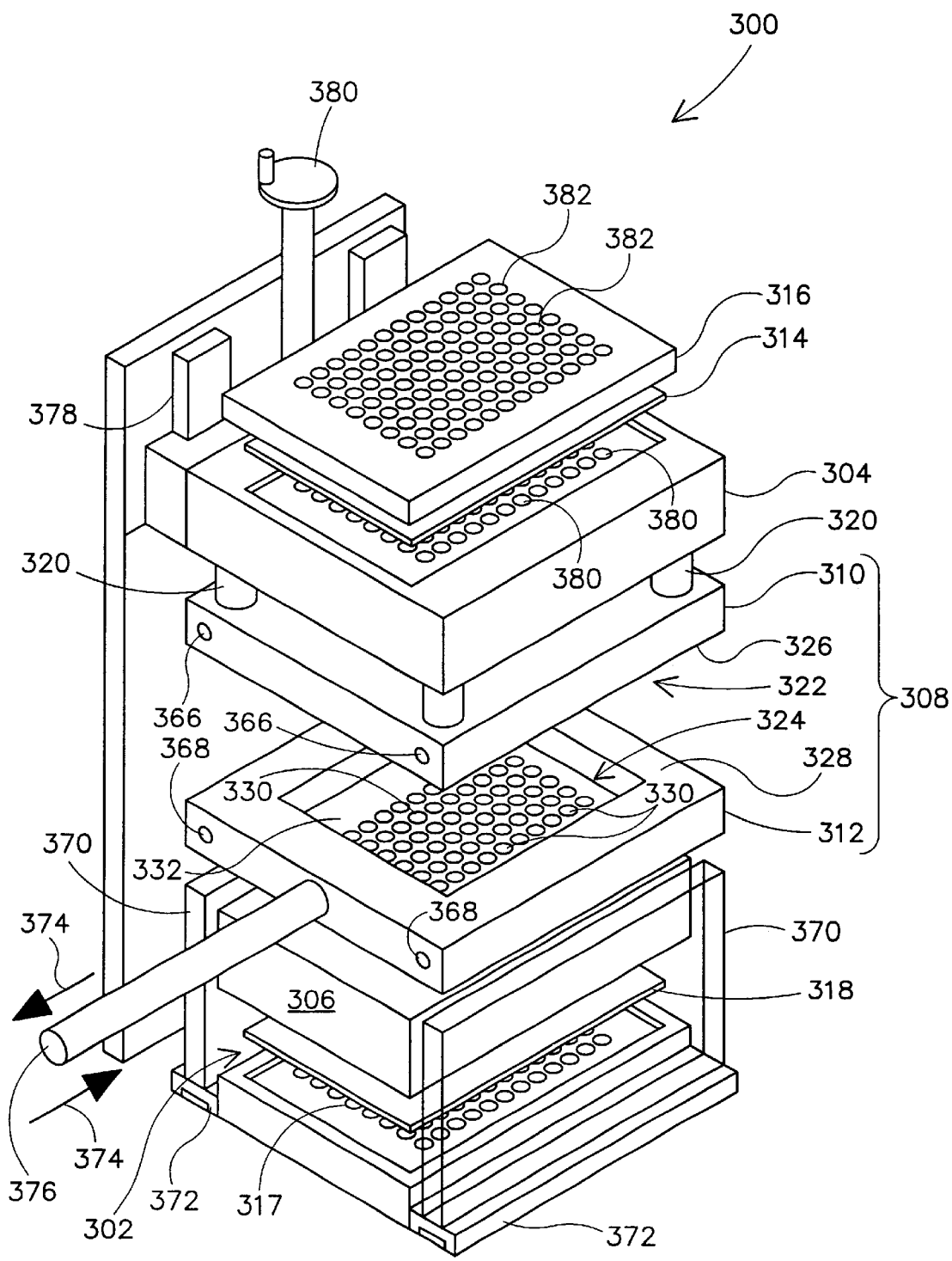
FIG. 13 is a perspective view of a rheo-optical indexer, which can be used to screen or characterize arrays of materials based on stress-induced birefringence measurements.

FIG. 13 shows a perspective view of an apparatus that can be used to screen or characterize arrays of materials based on stress-induced birefringence measurements. The rheo-optical indexer 300 comprises a monochromatic light source 302 having a first polarization direction. The indexer 300 includes an optical apparatus that collimates the light source into two or more parallel light beams and directs the parallel light beams through an array of materials or samples (not shown). In the embodiment shown in FIG. 13, the optical apparatus includes an upper collimator 304 and a lower collimator 306, which straddle a deformation device 308. The deformation device 308 includes an upper sample holder 310 and a lower sample holder 312, which contain the array of materials and subject the samples to mechanical deformation. The rheo-optical indexer 300 also includes an analyzing polarizer 314 having second polarization direction that is different than the first polarization direction, and a detector 316, which measures the intensity of light transmitted through the analyzing polarizer 314.

The monochromatic light source 302 may comprise one or more sources of unpolarized light—for example, a light bulb or a light table—together with a polarizing optical filter, such as polarizing film. Alternatively, the monochromatic light source may comprise a source of inherently polarized light, such as a laser or laser diode. In the embodiment shown in FIG. 13, the monochromatic light source 302 includes an array of light emitting diodes 317 (LED array) and a polarizing film 318. Suitable LED array 317 and polarizing film 318 are shown in FIG. 3. Other useful monochromatic light sources are discussed above.

As noted above, the rheo-optical indexer 300 shown in FIG. 13 includes an upper collimator 304 and lower collimator 306, that are disposed, respectively, above the upper sample holder 310, and below the lower sample holder 312. The upper collimator 304 does not rest directly on the upper sample holder 310; instead, standoffs 320 separate the upper collimator 304 from the upper sample holder 310. The standoffs 320 are fabricated from a thermally insulative material, which reduces heat transfer from the upper sample holder 310 to the upper collimator 304. Note, the upper 304 and lower 306 collimators are similar to the collimator block 130 shown in FIG. 4a and 4b, except they do not require the trough sections 138.

The upper 310 and lower 312 sample holders of the deformation device 308 are typically fabricated from a rigid material, such as aluminum, which has been black anodized to minimize light reflections. As shown in FIG. 13, both sample holders 310, 312 are rectangular blocks having wells 322, 324 formed on opposing surfaces 326, 328. The wells 322, 324 in the upper 310 and lower 312 sample holders are adapted and dimensioned to receive planar, non-birefringent windows (not shown). Apertures 330 arrayed along a bottom surface 332 of the well 324 formed in the lower sample holder 312, admit light from the lower collimator 306.

Figure 14:
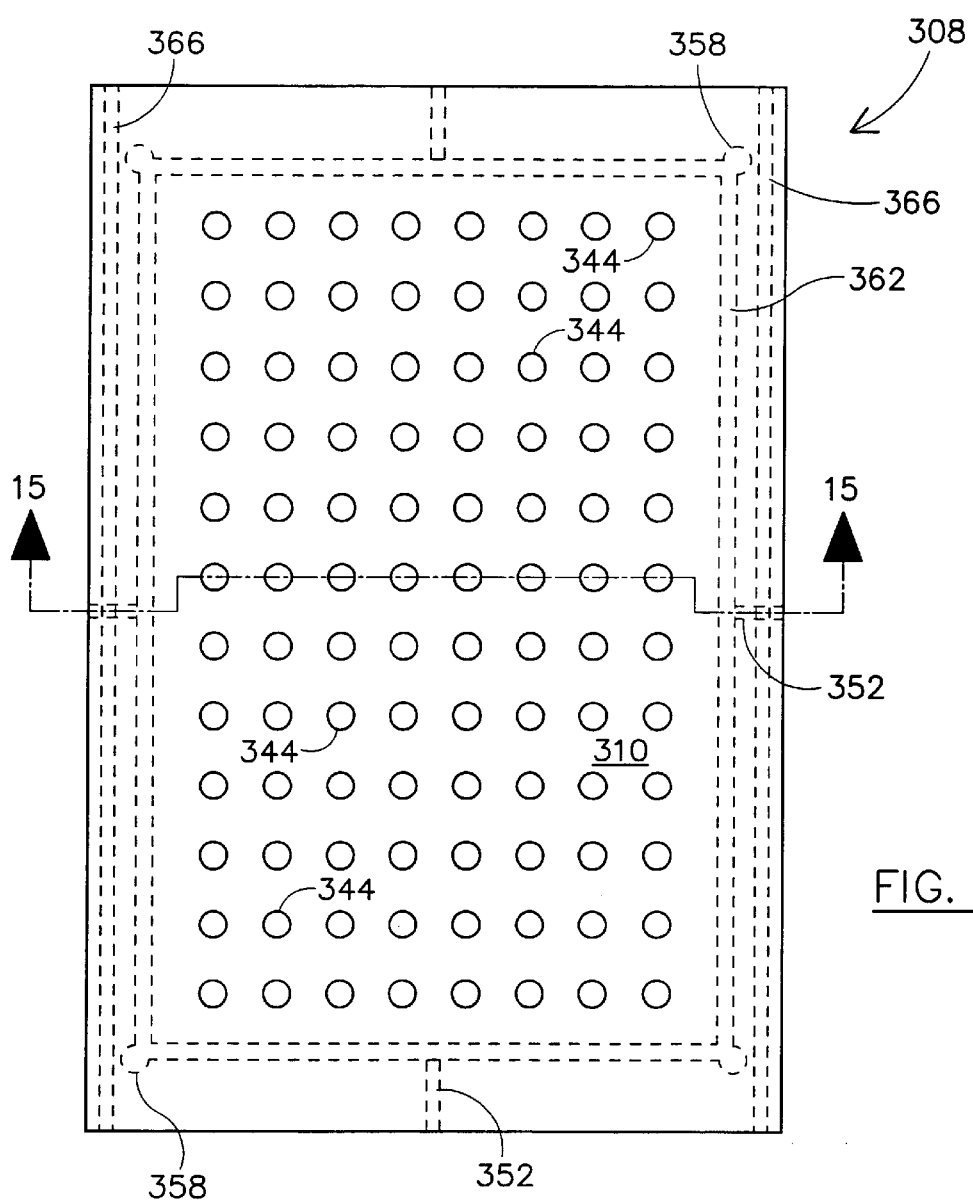
FIG. 14 is a bottom view of a deformation device, which is used to mechanically deform or shear arrays of material samples in the rheo-optical indexer of FIG. 13.
Figure 15:
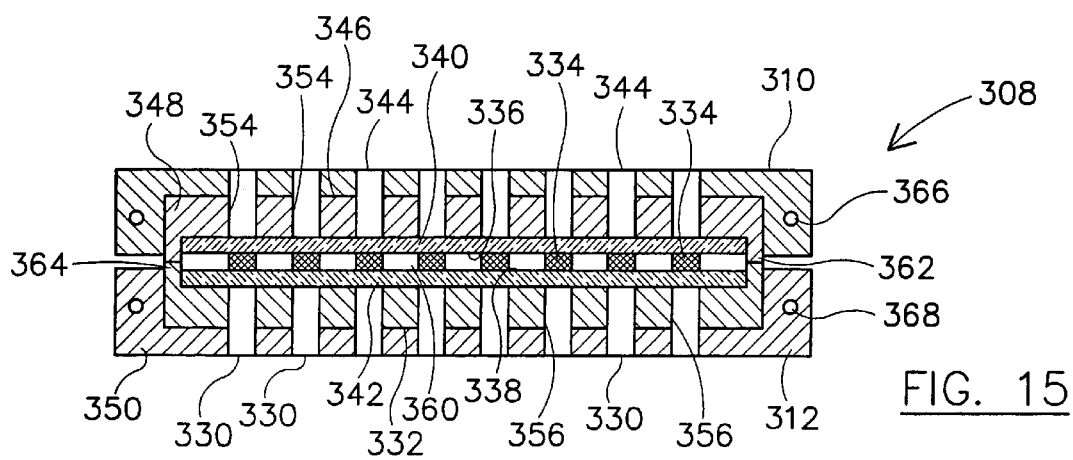
FIG. 15 is a cross sectional view of the deformation device shown in FIG. 14, which is used to mechanically deform or shear arrays of material samples in the rheo-optical indexer of FIG. 13.

FIG. 14 and 15 provide top and cross-sectional views, respectively, of the deformation device 308. Light entering the lower sample holder 312 through the array of apertures 330, passes through samples 334 captured between parallel and opposing planar surfaces 336, 338 of upper 340 and lower 342 non-birefringent windows. The light exits the deformation device 308 through another set of apertures 344 arrayed along a bottom surface 346 of the well 322 formed in the upper sample holder 310. The non-birefringent windows 340, 342 are mounted on rigid supports or plates 348, 350, which lessen the risk of damage to the windows 340, 342 during preparation and handling of the samples 334. The plates 348, 350, which are held in place with set screws 352, have apertures 354, 356, which are in substantial alignment with the samples 334 and the apertures 344, 330 in the upper 310 and lower 312 sample holders. The samples 334 are sized so they completely cover the apertures 354, 356 in the plates 348, 350. Corners 358 of the wells 322, 324 formed in the upper 310 and lower 312 sample holders are radiused to ease insertion of the non-birefringent windows 340, 342 and plates 348, 350 into the wells 322, 324. To shear the samples 334, the lower non-birefringent window 342 is translated in a plane parallel to the two opposing surfaces 336, 338, while the upper non-birefringent window 340 remains stationary.

Since the stress-optic coefficient—the proportionality constant relating stress to birefringence—is generally small for polymeric materials, the gap 360 or distance between the opposing surfaces 336, 338 of the upper 340 and lower 342 non-birefringent windows should be relatively large (~1 mm). One may set the size of the gap 360 between the two surfaces 336, 338 in various ways. For example, the gap 360 can be set by allowing the opposing surfaces 326, 328 of the upper 310 and lower 312 sample holders to touch during processing. In addition, prior to screening, one can set the size of the gap 360 by placing shims or other mechanical stops on the opposing surfaces 326, 328 of the upper 310 and lower 312 sample holders. Or as shown in FIG. 14 and 15, ridges 362, 364 along the periphery of the support plates 348, 350 can be used to set the gap 360. As discussed below, the gap 360 between the opposing surfaces 336, 338 of the upper 340 and lower 342 windows, and hence the thickness of the samples 334, can also be adjusted prior to and during screening using a vertical translation slide.

Because Theological characteristics of materials are generally strong functions of temperature, the deformation device 308 includes a system for controlling the temperature of the samples 334. For example, cylindrical holes 366, 368 are bored laterally through the sample holders 310, 312 and are dimensioned to receive cartridge heaters, which can be used to heat the samples 334. Other useful devices for controlling the temperature of the samples 334 are illustrated in FIGS. 7a–8b and are described in the text that accompanies the figures.

As noted above, the samples 334 shown in FIGS. 14 and 15 are sheared by translating the lower non-birefringent window 342 in a direction about normal to light entering the lower sample holder 312 through the array of apertures 330. To accomplish this motion, the lower sample holder 312 is attached to a pair of rigid supports 370, which are drawn in phantom in FIG. 13. The rigid supports 370 are mounted on horizontal translation slides 372, which allow the lower sample holder 312—and thus, the lower non-birefringent window 342—to move in a plane parallel to the two opposing surfaces 336, 338 of the upper 340 and lower 342 non-birefringent windows. The horizontal translation slides 372 are oriented such that translation occurs at 45 degrees with respect to the polarization direction of monochromatic light source 302. However, the apparatus 300 will operate with other orientations of the horizontal translation slides 372 as long as the resulting deformation of the samples 334 generate anisotropy that is neither parallel nor orthogonal to the polarization direction of monochromatic light source 302.

A pair of arrows 374 in FIG. 13 represents the direction of translation. A shaft 376 links the lower sample holder 312 to a drive mechanism (not shown), such as a DC motor; typically, a computer (not shown) controls the drive mechanism. As noted above, stress-optic coefficients for polymeric materials are typically small. So, the strain amplitude, which is the ratio of the gap 360 to the amplitude of the lateral displacement of the lower sample holder 312 relative to the upper sample holder 310, is often made relatively large (from about 0.1 to about 1.0) in order to produce a measurable signal. Although small strains simplify data analysis, the rheo-optical indexer often cannot operate with small strains because the resulting signal is insufficient.

Referring again to FIG. 13, the upper sample holder 310 and the upper collimator 304 are mounted on a vertical translation slide 378, which permits movement of the upper sample holder 310 and the upper collimator 304 in a direction normal to the lower sample holder 312. A micrometer screw 380 cooperates with the vertical translation slide 378 to adjust the gap 360 or separation distance between the opposing surfaces 336, 338 of the upper 340 and lower 342 non-birefringent windows (FIG. 14 and 15). In addition, the vertical translation slide 378 facilitates loading and unloading of the samples 334.

As noted above, the rheo-optical indexer 300 includes an analyzing polarizer 314 having second polarization direction that is different than the first polarization direction of the monochromatic light source 302. The analyzing polarizer 314 is disposed between the upper collimator 304 and the detector 316, and is typically a sheet of linearly polarizing material, such as a commercially available polarizing filter. The analyzing polarizer 314 is designed to block transmitted light having the same polarization direction as the incident polarized light originating from monochromatic light source 302. For stress-induced birefringence measurements, the analyzing polarizer 314 and the polarizing film 318 of the monochromatic light source 302 are usually oriented so the second polarization direction is orthogonal to the first polarization direction. When arranged in this manner, the analyzing polarizer 314 completely blocks transmitted light from the monochromatic light source 302—provided no depolarization or stress-induced birefringence occurs as light passes through the samples 334. However, one can obtain useful rheological data using non-orthogonal orientations, though a portion of light from the monochromatic light source 302 will pass through the analyzing polarizer 314 in the absence of any depolarization. For example, one may insert a quarter-wave plate immediately after the first polarizer 318 in order to convert the linearly polarized light transmitted through the first polarizer 318 into circularly polarized light. This maximizes the dependence of the intensity transmitted through the analyzing polarizer 314 on the depolarization of the samples 334. Although the use of a quarter wave plate increases the potential sensitivity of the instrument, it also results in a substantial rise in the intensity of light transmitted through the analyzing polarizer 314 even in the absence of any sample-induced depolarization.

The detector 316 measures the intensity of light transmitted through the analyzing polarizer 314, and outputs a signal corresponding to the intensity of light as a function of time. The signal can be recorded and analyzed using conventional signal processing equipment, including a computer equipped with a data acquisition board. Ordinarily, the detector 316 and the analyzing polarizer 314 are mounted on a rigid frame (not shown) so that, during screening, their positions remained fixed relative to the lower collimator 306 and the monochromatic light source 302. The detector 316 shown in FIG. 13 comprises an array of semiconductor photodetectors 382. Other useful detectors include discrete, non-imaging optical sensors, such as photomultipliers, and imaging systems, such as the human eye, film, or charge-coupled device (CCD).

The samples 334 shown in FIG. 15 are arrayed on predefined regions of the opposing surfaces 336, 338 of the upper 340 and the lower 342 non-birefringent windows so that the samples 334 are substantially aligned with the apertures 344, 330, 354, 356 in the upper 310 and lower 312 sample holders and the rigid support plates 348, 350. As indicated in FIGS. 13–15, the LED array 317 elements, the lower collimator 306 apertures (not shown), the slide holder 310, 312 apertures 344, 330, the rigid plate 348, 350 apertures 354, 356, the upper collimator 304 apertures 380, and the detector 382 elements are also substantially aligned. Thus, in the absence of the analyzing polarizer 314, light can pass virtually unobstructed from the monochromatic light source 302, through the samples 334, to the detector 316.

The array of samples 334 shown in FIG. 15 is typically prepared by depositing materials, either from solution or from melt, on predefined regions of the lower 342 window surface 338. Generally, if the array of samples 334 is prepared by solution deposition, the surface 338 is pretreated to prevent solutions from migrating from one predefined region to another. One useful surface pretreatment is to silane treat regions between the samples 334 as discussed in co-pending U.S. patent application "Formation of Combinatorial Arrays of Materials Using Solution-Based Methodologies," Ser. No. 09/156,827, and co-pending U.S. patent application "Polymer Libraries on a Substrate, Method of Forming Polymer Libraries on a Substrate and Characterization Methods With Same", Ser. No. 09/567,598, filed May 10, 2000, all of which are incorporated herein by reference. Arrays of samples may be of a desired size, such as 8 or more, 16 or more, 24 or more, 48 or more, and 96 or more samples and methods of forming such combinatorial libraries are described in U.S. Pat. Nos. 6,004,617 and 6,030,917 and co-pending U.S. Patent application "Apparatus and Method of Research for Creating and Testing Novel Catalysts, Reactions and Polymers", Ser. No. 09/227,558, filed Jan. 8, 1999, all of which are incorporated herein by reference. With either deposition technique, the array of samples 334 is usually annealed at a temperature greater than the glass transition temperature of the samples 334 for about twenty-four hours. Next, the upper window 340 is attached to the free surface of the samples 334, and the array of samples 334 is again annealed to eliminate any residual stresses.

During screening of combinatorial libraries, the samples 334 can be enclosed within an environmental chamber, similar to the chamber shown in FIG. 9. In addition, the samples 334 can be subjected to different electric fields and magnetic fields, in the manner shown in FIGS. 10–12 and the accompanying text.

The rheo-optical indexer 300 can be operated in at least two modes. In a first mode, the indexer 300 subjects the samples 334 simultaneously to an oscillatory mechanical deformation at a fixed frequency. The resulting birefringence is determined for each of the samples 334 and is compared to the deformation (strain) as a function of time to extract the in-phase and out-of-phase components of the birefringence. In addition, by measuring the phase lag of the birefringence signal relative to the mechanical deformation as a function of frequency, one can identify the frequency at which the in-phase and out-of-phase components have equal magnitude. In Theological measurements of polymer melts, the lowest such frequency at which this occurs is the "crossover frequency." The crossover frequency is associated with motion of the entire polymer chain and is a fundamental characteristic governing polymer processing and adhesion behavior.

In a second mode, the indexer 300 subjects the samples 334 simultaneously to a rapid, one-step strain, and the impulse response of each of the samples 334 is monitored. The impulse response can be used to determine the amount of stress-relaxation that occurs in a given amount of time, and to determine whether the samples 334 have non-relaxing stress. In addition, the impulse response can be used as an optical analog of a conventional melt-flow indexer.

Whether operated in the first mode or the second mode, the rheo-optical indexer 300 typically processes more than four-samples 334 an hour. Furthermore, the rheo-optical indexer typically processes more than eight samples 334 an hour. Moreover, the rheo-optical indexer often processes more than sixteen samples 334 an hour.

EXAMPLES

The following examples are intended as illustrative and non-limiting, and represent specific of embodiments of the present invention.

Example 1

Referring to FIGS. 16–21, to demonstrate depolarized scattering using an embodiment of the disclosed apparatus and method, the results of the characterization of a series of commercially available materials from Aldrich Chemical Company will be discussed. The materials consist of ethylene copolymerized with either methyl acrylate (MA) or vinyl acetate (VA). Table 1 lists characteristics of the copolymers, as reported by the supplier.

TABLE 1

Melting Temperatures for Polyethylene Copolymers

| Region | Comonomer | Melting Point (° C.) |
|---|---|---|
| H4 | 12 wt % VA | 95 |
| G2 | 6.5 wt % MA | 106 |
| E2 | 18 wt % VA | 87 |
| D4 | 9 wt % MA | 93 |
| C2 | 25 wt % VA | 75 |

Approximately 60 mg of the copolymers are individually provided in flat-bottom glass vials 6 mm in inner diameter with wall thickness of 1 mm. At low temperatures, all of these materials exhibit a birefringent morphology that includes crystalline polyethylene domains in a matrix of ethylene and either vinyl acetate or methyl acrylate segments. Upon heating above the melting point of the crystalline domains, the sample forms a spatially isotropic liquid and the birefringence disappears.

Once the material samples are placed in the vials, the vials are heated on a hot plate to about 140° C. to eliminate birefringent stresses associated with processing the material samples. The resulting material, in liquid form, adopts the shape of the vials, thereby forming a uniform plug approximately 2 mm in height. The vials are then removed from the hot plate and cooled to room temperature.

Once cooled, the vials are placed in regions 110 in sample block 102 and sample block 102 is positioned within the temperature controlled block 159 of FIG. 1. The light source 104 is directed at the material samples. The temperature controlled block 159 is then heated from about 70 to 120° C. at a rate of about 1.0° C./min. The intensity of the depolarized light beams transmitted through the vials is captured every two minutes by a lens-coupled CCD camera using an exposure time of 15 ms.

Figure 16:
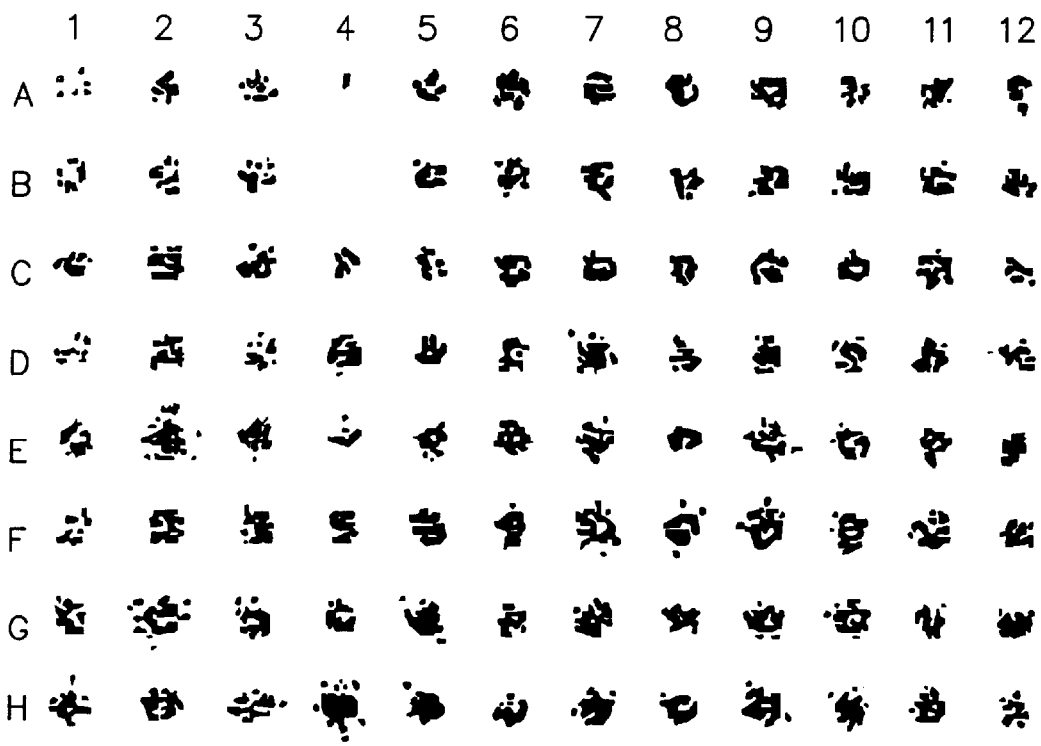
FIGS. 16–19 are negative images of the array of materials captured by a CDD camera at differing temperature intervals.

The resulting images captured by the CCD camera are shown in FIG. 16–19. FIG. 16 is a negative image of the array of material samples at 70° C. with a linear grayscale. Regions B4, C2, D4, E2, F4, G2 and H4 contain samples. All other regions are empty.

Figure 17:
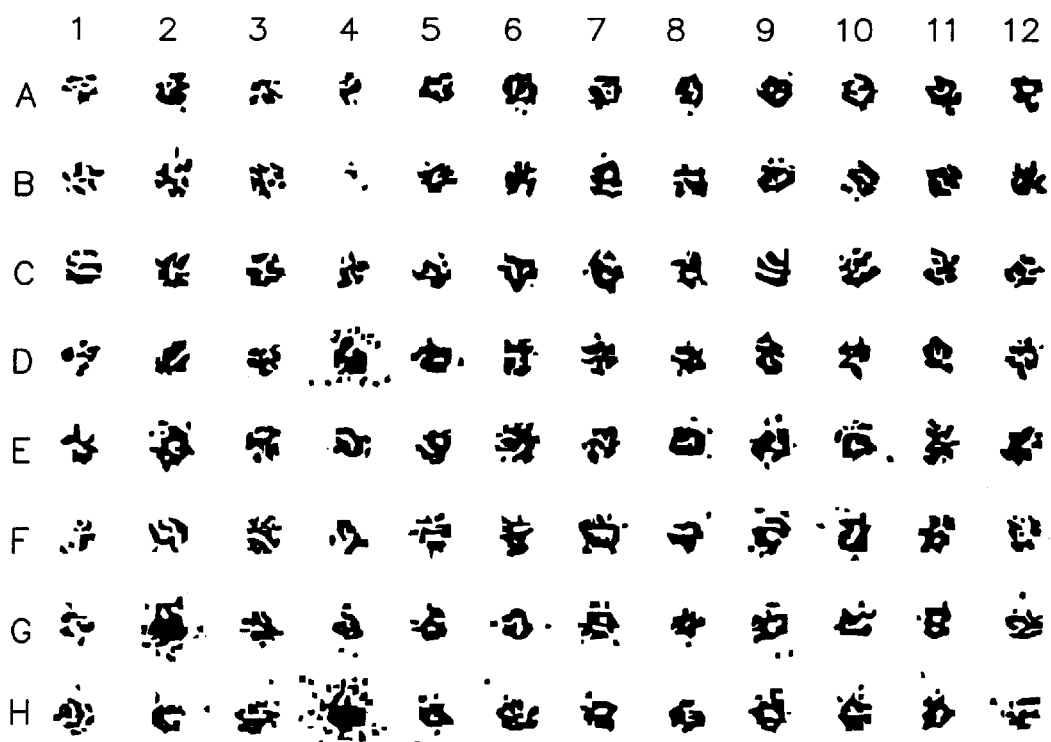

FIG. 17 is a negative image recorded at about 86° C. upon heating at about 1° C./min. As can be seen, regions C2 and F2 show a marked drop in intensity relative to the 70° C. image.

Figure 18:
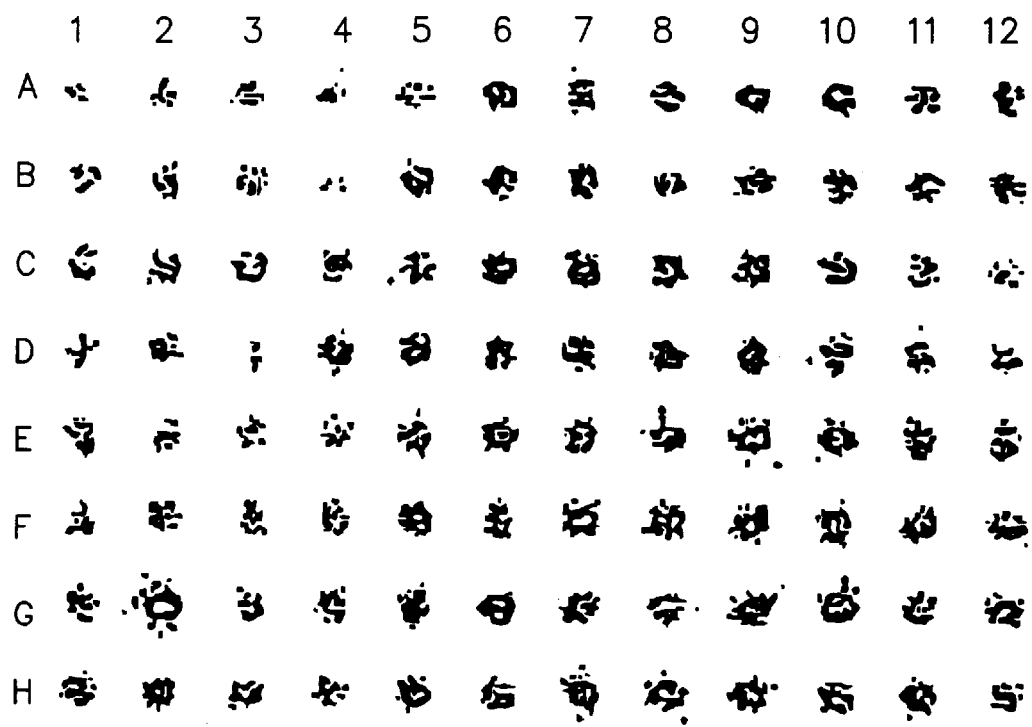
Figure 19:
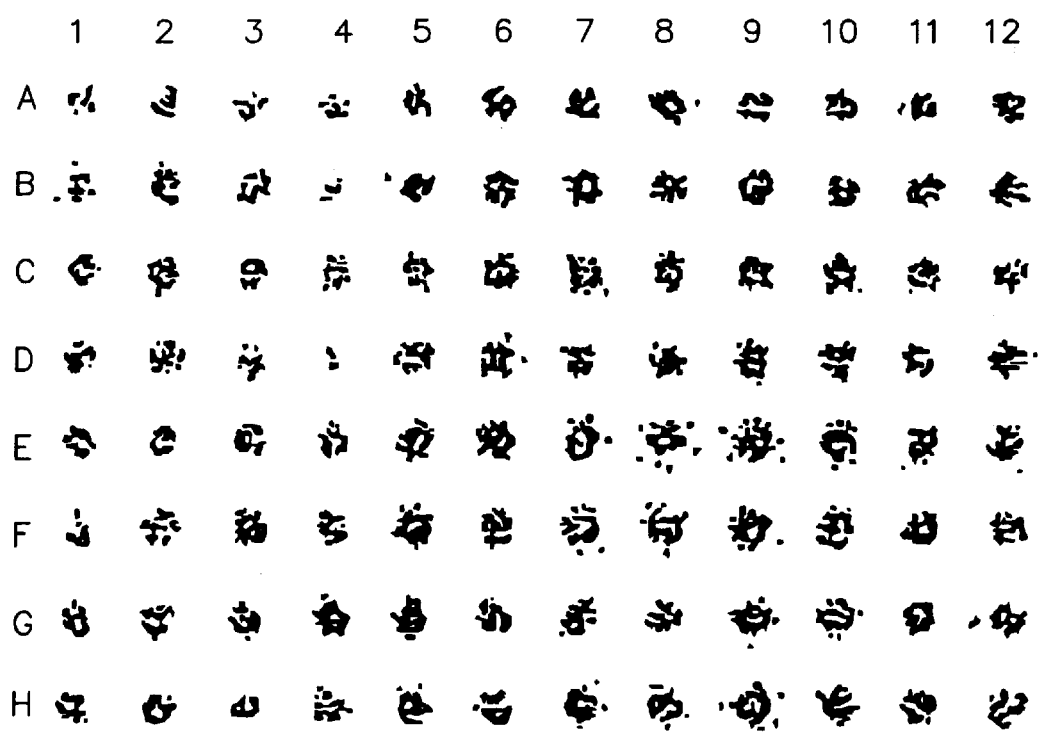

Referring to FIG. 18, at 102° C., only D4 and G2 exhibit a notable signal. However, upon reaching 116° C., all of the depolarization associated with the material samples has disappeared, indicating that all of the crystallites have melted, as can be seen in FIG. 19.

Figure 20:
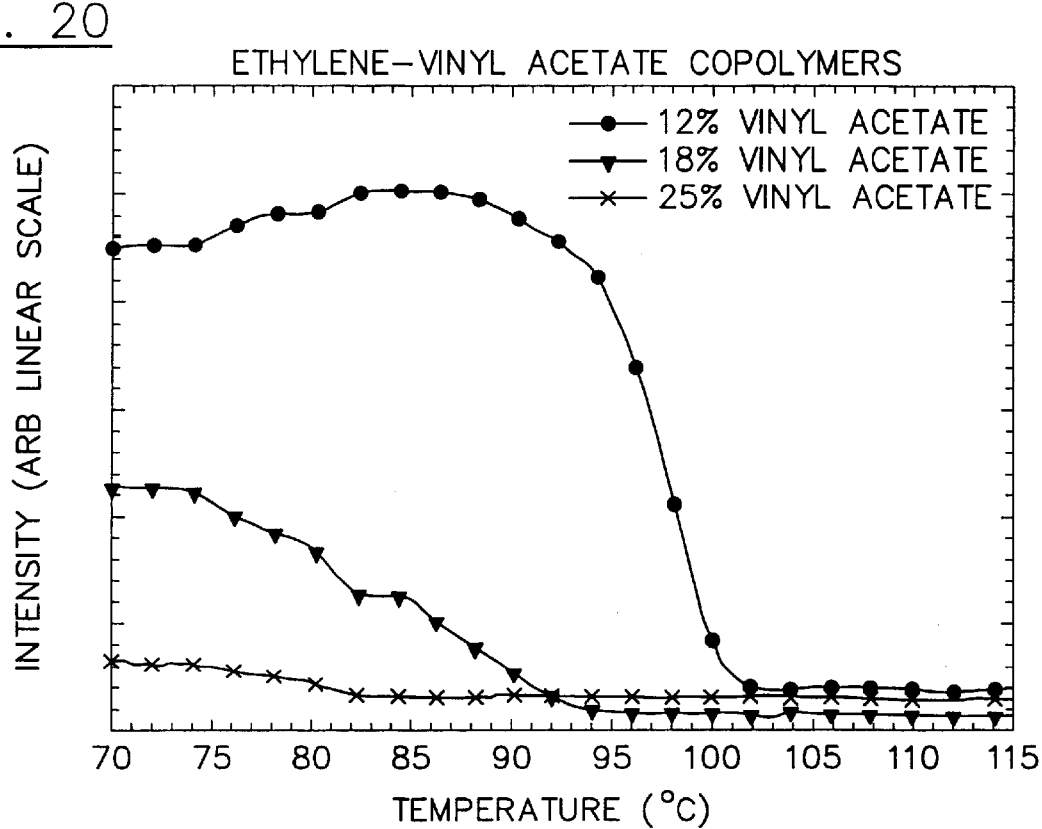
FIGS. 20–21 are graphical representations of the intensity readings of the array of materials as a function of temperature.

After the images of the material samples are captured by the CCD, the images can be digitized and analyzed, such as by suitable software. Graphical representations of the intensity data as a function of temperature are set out in FIG. 20 and 21. Referring to FIG. 20, the temperature dependence of the transmitted intensity for regions G2 (6.5 wt % methyl acrylate) and D4 (9.0 wt % methyl acrylate) are shown. For comparison, the intensity data for empty region F2 is also shown. For the VA copolymers, the measured transition temperature for the 6.5 wt % material sample corresponds to the value supplied by the supplier, as seen in Table 1. However, the value for the 9 wt % material sample is approximately ten degrees less than the value reported in Table 1. This discrepancy may reflect the presence of two different populations of crystallites. This hypothesis is supported by the differing slopes in the transition region (90–98° C. and 98–106° C., respectively).

Figure 21:
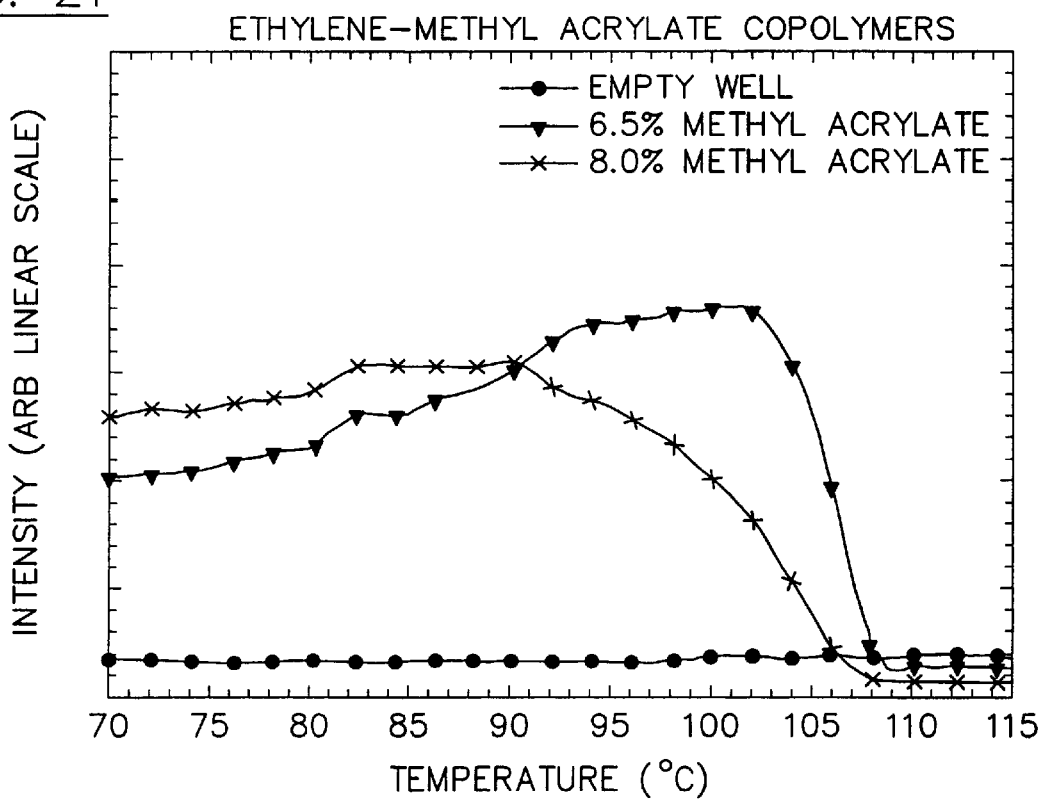

Referring to FIG. 21, the measured temperature dependence of the total intensity measured for regions H4 (12 wt % vinyl acetate), E2 (18 wt % vinyl acetate) and C2 (25 wt % vinyl acetate) of MA copolymers is depicted. The melting point is experimentally defined as the midpoint of the range in which the measured signal drops from the low-temperature value (approximated by a straight line) to the high-temperature value (also approximated by a straight line). Melting points identified in this manner generally correspond to the values reported by the supplier in Table 1, to within a few degrees. This discrepancy is comparable to that associated with the thermal gradients within the system. Further, the discrepancy may also reflect the use of a different heating rate as compared to the supplier's heating rate.

Preferred embodiments of the present invention have been disclosed. A person of ordinary skill in the art would realize, however, that certain modifications would come within the teachings of this invention. Therefore, the following claims should be studied to determine the true scope and content of the invention.

Example 2

A rheo-optical indexer similar to the instrument shown in FIG. 13–15 is used to characterize two polyisobutylene samples. The polyisobutylene samples are available from Polymer Standards Service, Mainz, Germany. Table 2 lists molecular weights of the two samples, as reported by the supplier.

TABLE 2

Molecular Weight of Polyisobutylene Polymers

| Sample | Weight-Average, $M_w$ g/mol | Number Average, $M_n$ g/mol |
| --- | --- | --- |
| 1 | 86,100 | 72,100 |
| 2 | 73,200 | 60,000 |

Referring to FIG. 15, flat glass plates, which serve as non-birefringent windows 340, 342, are mounted on perforated aluminum plates (rigid supports 348, 350) with five-minute epoxy. Approximately 5 mg samples of the polymers are placed at predefined locations on one of the mounted glass plates. The second mounted glass plate is placed on top of the first mounted glass plate and the two perforated aluminum plates are compressed until ridges 362, 364 located along the periphery of the support plates 348, 350 are brought into contact. This defines a gap 360 of about 100 μm. The resulting assembly is inserted into the well 324 of the lower sample holder 312 and the upper sample holder 310 is lowered into place so that the upper well 322 encloses the upper 348 support plate. Both support plates 348, 350 are locked against sides of the wells 322, 324 using set screws 352. The lower sample holder 312 is then translated relative to the upper sample holder 310 to bring the apertures 330, 344, 354, 356 into alignment. The two polymer samples are permitted to anneal at room temperature for at least an hour to remove any stresses induced by the sample preparation and loading procedure.

The rheo-optical indexer 300 of FIG. 13 deforms the polyisobutylene samples by translating the lower sample holder 312 and lower non-birefringent window 342 in a direction about normal to light entering the lower sample holder 312 through the array of apertures 330. The lower non-birefringent window 342 moves in a plane that is about parallel to the two opposing surfaces 336, 338 of the upper 340 and lower 342 non-birefringent windows shown in FIG. 15. Under the direction of a microprocessor-based controller (not shown), a motorized stage attached to the lower sample holder 312 translates the lower sample holder 312 in a sinusoidal manner at frequencies ranging from 0.1 to 10 radians/s. The translation amplitude, expressed as a fraction of the gap 360 thickness, is 2.0. An encoder (not shown), which is attached to the motorized stage, periodically monitors the position of the lower sample holder 312. The position of the lower sample holder 312 is recorded in the motor controller memory.

The rheo-optical indexer 300 measures stress-induced birefringence by monitoring changes in the intensity of light transmitted through the polyisobutylene samples. An amplified photodiode (detector 316) monitors the amount of light transmitted through the samples, and a commercially available A/D data acquisition board (not shown) records light intensity as a function of time. To synchronize light intensity data with the position of the lower sample holder 312, the motor controller sends a timing pulse to the A/D board to trigger data acquisition. Ten waveforms are recorded at each deformation frequency, at a resolution of one-hundred acquisitions per waveform. The resulting position and intensity curves are compared to extract the amplitude and relative phase of the intensity signal. This amplitude is divided by the amplitude of the position waveform and is used as a measure of the stress-optic shear modulus. The resulting modulus is subdivided into in-phase and out-of-phase contributions by multiplying by the cosine and sine of the relative phase, respectively.

FIG. 22 and 23 show the in-phase (E') and out-of-phase (E") components of the stress-optic shear modulus as a function of frequency for Samples 1 and 2 listed in Table 2. At high frequencies, the response of both polymers is nearly independent of frequency and is dominated by the in-phase contribution, as expected for a highly entangled polymer melt. At moderate frequencies, both samples show a crossover from elastic (in-phase) behavior to viscous (out-of-phase) behavior. The location of the crossover decreases with increasing molecular weight, as expected, and the ratio of the crossover frequencies is roughly proportional to the 3.4 power of the ratio of molecular weights. At lower frequencies the viscous, out-of-phase modulus dominates the samples' behavior. In this regime, both polymers show an approach toward terminal relaxation behavior in which the in-phase contribution varies with the square of the frequency, and the out-of-phase term varies linearly with frequency.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. An apparatus for measuring rheological properties of a plurality of material samples, the apparatus comprising:

first and second surfaces defining a substantially uniform gap for containing the plurality of material samples, the first and second surfaces being generally planar and capable of transmitting light;

a device for moving the first and second surfaces relative to each other so as to exert a shear stress on the plurality of material samples contained in the gap;

a source of light having a first polarization direction, and an analyzer having a second polarization direction, the source of light and the analyzer located on opposite sides of the gap so that light from the source passes through the plurality of material samples contained in the gap before striking the analyzer; and a detector associated with the analyzer for detecting light from the source, the light from the source having passed through the plurality of material samples and the analyzer;

wherein the detector is capable of distinguishing light transmitted through at least two of the material samples simultaneously.

2. The apparatus of claim 1, wherein the light source comprises an unpolarized light source and a polarizing filter.

3. The apparatus of claim 2, wherein the unpolarized light source is a light table.

4. The apparatus of claim 2, wherein the unpolarized light source is an array of light emitting diodes.

5. The apparatus of claim 1, wherein the light source comprises a laser.

6. The apparatus of claim 1, wherein the light source comprises an array of laser diodes.

7. The apparatus of claim 1 further comprising a first collimator for directing light from the source to the plurality of material samples, the first collimator disposed between the light source and the gap.

8. The apparatus of claim 1 further comprising a second collimator for directing light passing through the plurality of samples to the analyzer, the second collimator disposed between the gap and the analyzer.

9. The apparatus of claim 1 further comprising a translation slide for adjusting the gap between the first surface and the second surface.

10. The apparatus of claim 1, wherein the analyzer comprises a polarizing filter.

11. The apparatus of claim 1, wherein the first polarization direction is orthogonal to the second polarization direction.

12. The apparatus of claim 1, wherein the detector comprises an array of non-imaging optical sensors.

13. The apparatus of claim 12, wherein the non-imaging optical sensors are photomultipliers.

14. The apparatus of claim 12, wherein the detector comprises an array of semiconductor photodetectors.

15. The apparatus of claim 1, wherein the detector is an imaging system.

16. The apparatus of claim 15, wherein the imaging system comprises a charge-coupled device.

17. The apparatus of claim 1 further comprising an environmental chamber enclosing the gap.

18. The apparatus of claim 1, wherein the detector is capable of distinguishing light transmitted through at least four of the material samples simultaneously.

19. The apparatus of claim 1, wherein the detector is capable of distinguishing light transmitted through at least eight of the material samples simultaneously.

20. The apparatus of claim 1 further comprising a quarter-wave plate for generating circularly polarized light, the quarter-wave plate located between the light source and the gap.

21. The apparatus of claim 1 further comprising a system for controlling the temperature of the plurality of material samples.

22. A method of screening an array of materials, the method comprising:

providing an array of materials, the array of materials comprising discrete material elements;

illuminating the array of materials with light having a first polarization direction;

shearing the array of materials by deforming each of the discrete material elements in a direction normal to the light illuminating the array of materials;

directing the light transmitted through the array of materials through an analyzer, the analyzer having a second polarization direction; and detecting changes in intensity of the light passing through the analyzer from at least two of the discrete material elements simultaneously.

23. The method of claim 22, wherein during shearing the first polarization direction is orthogonal to the second polarization direction.

24. The method of claim 22, wherein during shearing each of the discrete material elements undergo an oscillatory deformation.

25. The method of claim 24, further comprising comparing the oscillatory deformation with the intensity of light passing through the discrete material elements to extract in-phase and out-of-phase components of the changes in the intensity of light.

26. The method of claim 25, further comprising measuring a phase lag of the changes in the intensity of light relative to the oscillatory deformation of each of the discrete material elements.

27. The method of claim 22, wherein during shearing each of the discrete material elements undergo a one-step strain.

28. The method of claim 22, further comprising detecting changes in intensity of light passing through the analyzer from at least four discrete material elements simultaneously.

29. The method of claim 22 further comprising controlling the temperature of the array of materials.

30. The method of claim 22 further comprising enclosing the array of materials in an environmental chamber.

31. A method of screening an array of materials, the method comprising:

providing an array of materials comprised of discrete material elements spanning a substantially uniform gap between a first surface and a second surface;

passing light having a first polarization direction through the first and second surfaces and the array of materials;

moving the first and second surfaces relative to each other so as to exert a shear stress on the discrete material elements spanning the gap;

directing light passing through the array of materials through an analyzer, the analyzer having a second polarization direction; and detecting changes in intensity of the light passing through the analyzer from at least two of the discrete material elements simultaneously.

32. The method of claim 31, wherein providing the array of materials comprises disposing at least four discrete material elements between the first surface and the second surface.

33. The method of claim 31, wherein during shearing the first polarization direction is orthogonal to the second polarization direction.

* * * * *